United States Patent
Kippersund et al.

(10) Patent No.: US 10,317,262 B2
(45) Date of Patent: Jun. 11, 2019

(54) SENSOR APPARATUS

(71) Applicant: XSENS AS, Bergen (NO)

(72) Inventors: Remi Andre Kippersund, Bergen (NO); Magne Kjetil Husebø, Tertnes (NO); Per Lunde, Sandsli (NO); Kjell-Eivind Frøysa, Fryllingsdalen (NO); Peter Thomas, Rådal (NO); Kjetil Daae Lohne, Bønes (NO); Jon Hellevang, Bergen (NO)

(73) Assignee: XSENS AS, Bergen (NO)

( * ) Notice: Subject to any disclaimer, the term of this patent is extended or adjusted under 35 U.S.C. 154(b) by 62 days.

(21) Appl. No.: 15/108,527

(22) PCT Filed: Dec. 29, 2014

(86) PCT No.: PCT/EP2014/003474
§ 371 (c)(1),
(2) Date: Jun. 27, 2016

(87) PCT Pub. No.: WO2015/096902
PCT Pub. Date: Jul. 2, 2015

(65) Prior Publication Data
US 2016/0320219 A1    Nov. 3, 2016

(30) Foreign Application Priority Data
Dec. 27, 2013   (GB) .................. 1323076.8

(51) Int. Cl.
*G01F 1/66*      (2006.01)
*G01F 1/74*      (2006.01)
(Continued)

(52) U.S. Cl.
CPC ............. *G01F 1/662* (2013.01); *G01F 1/66* (2013.01); *G01F 1/663* (2013.01); *G01F 1/667* (2013.01);
(Continued)

(58) Field of Classification Search
CPC ............................................ G01F 1/662
See application file for complete search history.

(56) References Cited

U.S. PATENT DOCUMENTS 6,047,602 A * 4/2000 Lynnworth ............. G01F 1/662
                                                        73/632
6,089,104 A   7/2000 Chang
(Continued)

FOREIGN PATENT DOCUMENTS

CN     203132615 U    8/2013
DE   102011015677 A1  10/2012
(Continued)

OTHER PUBLICATIONS

Cho, H., Tamura, Y. & Matsuo, T. J Nondestruct Eval (2011) 30: 59. https://doi.org/10.1007/s10921-011-0090-z.*
(Continued)

*Primary Examiner* — Son T Le
*Assistant Examiner* — Alexander A Mercado
(74) *Attorney, Agent, or Firm* — Arent Fox LLP

(57) ABSTRACT

A sensor apparatus is provided for measuring characteristics of a wall of a structure and/or a medium in contact with the structure, wherein the sensor apparatus includes a transducer arrangement disposed at least partially around a planar or curved surface of a wall of the structure, or disposed over a region of a planar or curved surface of a wall of the structure. The sensor apparatus includes a transducer waveguide including at least one free distal end whereat one or more driver and/or receiver elements are mounted on one or more sides of the at least one free distal end. Moreover, the transducer arrangement is operable, when interrogating the structure to perform at least one of: switching between selected acoustic wave modes present in an acoustic wave
(Continued)

propagation, steering an acoustic propagation direction of the acoustic wave propagation.

21 Claims, 17 Drawing Sheets

(51) Int. Cl.
  *G01P 5/00* (2006.01)
  *G01N 29/22* (2006.01)
(52) U.S. Cl.
  CPC ............... *G01F 1/74* (2013.01); *G01N 29/22* (2013.01); *G01P 5/001* (2013.01); *G01N 2291/0289* (2013.01); *G01N 2291/02433* (2013.01)

(56) References Cited

U.S. PATENT DOCUMENTS

| | | | |
|---|---|---|---|
| 6,100,969 A * | 8/2000 | Perez | G01N 21/1702 356/73.1 |
| 7,185,547 B2 | 3/2007 | Baumoel | |
| 8,090,131 B2 | 1/2012 | Lynnworth | |
| 2002/0053243 A1 | 5/2002 | Su | |
| 2003/0121335 A1 | 7/2003 | Liu et al. | |
| 2006/0144162 A1 | 7/2006 | Batzinger et al. | |
| 2008/0156107 A1 | 7/2008 | Ao et al. | |

FOREIGN PATENT DOCUMENTS

| | | |
|---|---|---|
| EP | 2369334 A1 | 9/2011 |
| FR | 2781047 A1 | 1/2000 |
| GB | 2399412 A | 9/2004 |
| GB | 2412966 A | 10/2005 |
| GB | 2479115 B | 10/2011 |
| NO | 331687 B1 | 2/2012 |
| WO | 98/19296 A1 | 5/1998 |
| WO | 2008/073673 A1 | 6/2008 |
| WO | 2010/118793 A1 | 10/2010 |
| WO | WO 2011/078691 A2 | 8/2011 |
| WO | WO 2014/098613 A1 | 6/2014 |

OTHER PUBLICATIONS

Leonard, Kevin, et al., "Guided Wave Helical Ultrasonic Tomography of Pipes", The Journal of the Acoustical Society of America, vol. 114, No. 2, Aug. 2003, pp. 767-774.

Shelke, Amit, et al., "Mode-selective excitation and detection of ultrasonic guided waves for delamination detection in laminated aluminum plates", IEEE Transactions on Ultrasonics, Ferroelectrics, and Frequency Control, vol. 58, Issue 3, Mar. 17, 2011, pp. 567-577.

Majumder, Mousumi, et al., "Fibre Bragg gratings in structural health monitoring—Present status and applications", Elsevier, Sensors and Actuators A: Physical, vol. 147, Issue 1, Sep. 15, 2008, pp. 150-164.

International Search Report and Written Opinion received for International Patent Application No. PCT/EP2014/003474, dated Jun. 18, 2015, 15 pages.

International Preliminary Report on Patentability received for International Patent Application No. PCT/EP2014/003474, dated Apr. 15, 2016, 43 Pages.

Written Opinion received for International Patent Application No. PCT/EP2014/003474, dated Dec. 8, 2015, 10 pages.

Combined Search and Examination Report received for United Kingdom Patent Application No. GB1323076.8, dated Apr. 8, 2014, 8 pages.

\* cited by examiner

SENSOR APPARATUS

TECHNICAL FIELD

The present disclosure relates to sensor apparatus, for example to sensor apparatus for exciting and/or receiving acoustic radiation from a mechanical structure, for example a planar structure, a curved structure, a vessel or a conduit; the conduit is, for example, implemented as a pipe. Moreover, the present disclosure also concerns methods of using aforesaid sensor apparatus for interrogating the aforementioned mechanical structure. Furthermore, the present disclosure relates to computer program products comprising a non-transitory computer-readable data storage medium having computer-readable instructions stored thereon, the computer-readable instructions being executable by a computerized device comprising processing hardware to execute the aforesaid methods.

BACKGROUND

Many situations in industry, for example in food processing industries, chemical industries, petrochemicals industry and nuclear power industry, require interrogation of a mechanical structure, for example, vessel or conduit, for example a pipe or pipeline, to measure characteristics of gases, fluids and/or solids in contact with the mechanical structure, as well as an integrity of the mechanical structure itself. For example, the gases, fluids and/or solids potentially cause pressure build-up within the mechanical structures, blockages and even corrosion and/or embrittlement of the structure.

In a United Kingdom patent document GB2 399 412A ("Multiple phase fraction meter having compliant mandrel deployed within fluid conduit", Applicant—Weatherford/Lamb Inc.), there is described a hollow mandrel which is deployable within a production pipeline at least partly within a length of a speed of sound or phase fraction meter. Sensors of the meter comprise Bragg gratings and wraps of fibre optic cable whose lengths are sensitive to acoustic pressure disturbances in the pipeline. A passive fibre optic based flow velocity meter is thereby provided, and the mandrel is optionally shaped to form an annular venture meter to provide an alternative implementation for calculating the fluid mixture density for purposes of double checking or calibration.

In a published US patent document U.S. Pat. No. 6,047,602 ("Ultrasonic buffer/waveguide", Applicant—Panametrics Inc.), there is described a waveguide for coupling ultrasonic energy from a source on one side of a fluid-bounding wall, such as a conduit, into fluid on the other side of the wall. The waveguide has a buffer that couples to the source, and a seat with an exit face, and an intermediate portion includes a redirecting surface for internally redirecting energy propagated along the buffer towards the exit face to exit as a narrow directed beam. The waveguide core has a rectangular cross-section which is narrow, namely has an aspect ratio above two, and the buffer has a length which is effective to isolate thermally and to protect the source from the conduit. The waveguide is attached via clamp-on or welding to a pipe or spool-face. Optionally, the buffer is a thin tube which couples shear waves into the seat portion, which has a rectangular cross-section.

In a published United States patent document U.S. Pat. No. 7,185,547B2 ("Extreme temperature clamp-on flow meter transducer", applicant—Siemens Energy and Automation Inc.), there is described a device for measuring flow in a pipe. The device includes a first metal plate mounted to the pipe. The first metal plate includes a first contact portion for contacting a wall of the pipe and a first away portion spaced apart from the wall of the pipe. The device further includes a second plate including a second contact portion spaced apart from the wall of the pipe. A first transducer is mounted to the first away portion. Moreover, a second transducer is mounted to the second away portion. The first and second transducers are thereby mounted spatially remotely from the wall of the pipe. The device provides an operational benefit that the first and second transducers are acoustically coupled via associated curved strips disposed between the contact portions and the away portions, thereby providing the transducers with a degree of isolation from the pipe. Such benefit assists when the pipe includes a flow of fluid therein a high temperatures.

In a published US patent document U.S. Pat. No. 8,090,131 B2 ("Steerable acoustic waveguide", Applicant—Elster NV/SA), there is described a steerable acoustic waveguide apparatus which includes a plurality of plates arranged in one or more linear arrays. Steering of an acoustic beam radiated from the waveguide apparatus may be achieved through differential delays of acoustic signals resulting from differences in timing, frequency, or mode or resulting from difference in physical attributes of the plates. The waveguide apparatus serves as a thermal buffer, and may simplify access to an acoustic path in a device such as an ultrasonic flow meter.

Referring to FIG. 9, an off-shore environment is indicated generally by 10, wherein a sea-bed assembly 20 is submerged in water 15, and is coupled via one or more sea-bed pipelines 25 to a petrochemicals processing facility 30. The assembly 20 is alternatively, or additionally, coupled via the one or more pipelines 25 to a floating oil platform (not shown). The sea-bed assembly 20 is coupled via a bore hole 35, for example defined by a liner tube, to a subterranean anticline including oil and/or gas resources. In many situations, the sea-bed assembly 20 is more than 1 km deep in the water 15 and is potentially subject to pressure of 150 Bar or more. An environment experienced by the sea-bed assembly 20 is challenging for any type of sea-bed assembly 20 and associated one or more pipelines 25. Blockages, corrosion, scale deposits, leaks and similar occurring within or along the one or more pipelines 25 can potentially compromise operation of the sea-bed assembly 20 and the associated one or more pipelines 25, for example in a event of a leak or unexpected pressure surge from the anticline. Known types of sensor apparatus are not able to provide suitable measurement flexibility and yet be able to withstand, over a long period of use, harsh environmental conditions associated with operation of the sea-bed assembly 20.

In a published international PCT patent document WO2014/098613A1 ("Sensor System for Corrosion Monitoring", Applicant—TeCom AS), there is described a sensor system for monitoring corrosion in a wall of a pipeline or vessel. The sensor system includes at least one acoustic emitter. Moreover, the sensor system includes an optical fibre provided with an arrangement for converting an acoustic signal to a corresponding optical signal. During operation, the at least one acoustic emitter emits a beam of acoustic radiation which is then reflected as a corresponding reflected beam which is received by the optical fibre to provide information for the optical signal. A sensitive material of the optical fibre allows for corrosion-related chemical parameters to be measured in a continuous fashion over a length of the optical fibre. The chemical parameters relate to at least one of: liquid water, humidity, salinity, pH and electrical conductivity. The arrangement for converting the acoustic signal to the corresponding optical signal is based upon the use of Bragg filter gratings.

SUMMARY

The present disclosure seeks to provide an improved sensor apparatus for measuring a mechanical structure, for example a vessel or conduit, for example within the mechanical structure, for measuring structural characteristics of the structure, for example an integrity of the structure.

Moreover, the present disclosure seeks to provide a method of using an improved sensor apparatus, for measuring a mechanical structure, for example a vessel or conduit, for example within the mechanical structure, for measuring structural characteristics of the structure, for example an integrity of the structure.

According to a first aspect, there is provided a sensor apparatus for measuring characteristics of a wall of a structure and/or a medium in contact with the structure, wherein the sensor apparatus includes a transducer arrangement disposed at least partially around a planar or curved surface of a wall of the structure, or disposed over a region of a planar or curved surface of a wall of the structure,
characterized in that
the sensor apparatus includes a transducer waveguide including at least one free distal end whereat one or more driver and/or receiver elements are mounted on one or more sides of the at least one free distal end;
the transducer arrangement is operable, when interrogating the structure to perform at least one of: switching between selected acoustic wave modes present in an acoustic wave propagation, steering an acoustic propagation direction of the acoustic wave propagation; and
wherein the one or more driver elements are operable to excite the acoustic wave propagation within the wall of the structure (for providing information indicative of properties of the wall and/or material present in a vicinity of the wall which interacts with the acoustic wave propagation.

The invention is of advantage in that the sensor apparatus is capable of interrogating the mechanical structure in a more thorough manner than has hitherto been possible on account of flexibility of operation provided by its transducer arrangement, for example on account of the transducer arrangement being operable to generate cleaner selectable acoustic modes in the mechanical structure which are selectively steerable in direction.

Optionally, in the sensor apparatus, the transducer arrangement includes a waveguide arrangement which is operable to excite a helical acoustic wave propagation within the mechanical structure, implemented to include at least one curved wall, from the one or more driver elements disposed at one or more ends of the waveguide arrangement.

Optionally, in the sensor apparatus, the one or more driver and/or receiver elements of the transducer waveguide are operable to select one or more specific modes of acoustic radiation propagation by exciting a predominantly through-thickness stress/displacement signature for the one or more specific modes. More optionally, in the sensor apparatus, the one or more driver elements are configurable by selectively exciting them to switch between acoustic radiation modes.

Optionally, in the sensor apparatus, the switching between the acoustic radiation modes is achieved by selectively switching between in-phase and out-of-phase excitation of elements on upper and lower faces of one or more distal ends of the transducer waveguide, thereby enabling switching between symmetrical and anti-symmetrical acoustic radiation modes in the transducer waveguide.

Optionally, in the sensor apparatus, the one or more elements have a bandwidth which is sufficient to enable the transducer waveguide to emit acoustic radiation which has a similar dispersion characteristic to a material of the a wall of a structure and/or a medium in contact with the structure.

Optionally, in the sensor apparatus, the one or more elements are operable to utilize broadband signals, which are efficiently transmitted to the wall of the structure as the transducer waveguide has a similar dispersion characteristic as the wall of the structure.

Optionally, in the sensor apparatus, the one or more driver and/or receiver elements are disposed in an array configuration comprising a plurality of elements, for enabling an amplitude and/or direction of acoustic modes propagating in the transducer waveguide to be steered.

Optionally, in the sensor apparatus, a steering angle and/or amplitude of one or more modes excited in the transducer waveguide are monitored by additional one or more sensors attached to the transducer waveguide.

Optionally, in the sensor apparatus, the transducer waveguide is implemented as at least of: a sheet of material, a strip, a collar, an annulus, a helical elongate member, a helical strip, a component formed into the wall of the structure.

Optionally, in the sensor apparatus, the one or more receiver elements are implemented optically using one or more Bragg grating sensors. More optionally, in the sensor apparatus, the one or more Bragg grating sensors are formed in one or more silica monomode optical fibres or sapphire monomode optical fibres.

Optionally, in the sensor apparatus, the one or more driver and/or receiver elements are provided with a shielding arrangement for shielding them from thermal and/or ionizing radiation emitted from the structure.

Optionally, in the sensor apparatus, the transducer waveguide is detachably mountable to the structure.

Optionally, in the sensor apparatus, the transducer waveguide has a substantially similar thickness to the wall of the structure, and is fabricated from a material which is substantially similar to that of the wall of the structure. More optionally, in the sensor apparatus, the transducer waveguide is fabricated from at least one of: a metal, a ceramic, a piezoelectric ceramic material, a composite material, a sintered material.

Optionally, the sensor apparatus further includes a data processing arrangement for generating drive signals to drive the one or more driver elements for selectively interrogating one or more regions adjacent to the wall of the structure, and the data processing arrangement is operable to receive signals from the one or more regions, and to perform tomographic (tomometric) computation upon the information to indentify, in respect of the wall, at least one of: a scale or hydrate deposit on the wall, erosion and/or corrosion of the wall, cracking of the wall. More optionally, in the sensor apparatus, the one or more regions are selectively interrogated by varying an amplitude and/or a relative phase of one or more drive signals applied to the one or more driver elements.

Optionally, the sensor apparatus further includes one or more environmental sensors disposed in a region between an outer surface of the wall of the structure and a cladding of the structure, wherein the one or more environmental sensors are disposed remotely in respect of the transducer waveguide and are operable to receive acoustic radiation coupled along the wall of the structure to the one or more environmental sensors. More optionally, in the sensor apparatus, the one or more environmental sensors are operable measure chemical parameters relating to at least one of: liquid water, humidity, salinity, pH and electrical conductivity. More optionally, in the sensor apparatus, the transducer waveguide and the one or more environmental sensors employ a common optical fibre with sensors formed therealong for sensing purposes.

Optionally, in the sensor apparatus, at least one transducer waveguide of the transducer arrangement includes a first end thereof and a second end thereof, wherein an array of transducer elements is disposed at the first end and are individually excitable in a phase-array manner for steering the one or more beams within the region. More optionally, in the sensor apparatus, the at least one waveguide of the transducer arrangement includes one or more transducer elements disposed at the second end for receiving temporarily short pulses for monitoring integrity of operation of the waveguide and/or for enabling a temperature compensation to be applied by a signal processing arrangement for operation of the waveguide.

Optionally, in the sensor apparatus, the transducer arrangement includes a spatially distributed array of sensors disposed on an external surface of the wall for receiving acoustic radiation coupled through the wall thereto. More optionally, in the sensor apparatus, the spatially distributed array of sensors is interspersed between waveguides of the transducer arrangement for generating the one or more beams. More optionally, in the sensor apparatus, the spatially distributed array of sensors is implemented using a plurality of Bragg grating filter sensors distributed along one or more optical fibres, wherein the Bragg filter sensors are optically interrogated in operation via optical radiation guided through the one or more optical fibres and selectively reflected and/or transmitted at the Bragg grating filter sensors (FBG).

Optionally, in the sensor apparatus, the transducer arrangement includes one or more interfacing components which enabled the transducer arrangement to be excited from one or more optical signals conveyed via one or more optical fibres coupled to the sensor apparatus and/or to output its received acoustic radiation signals via the wall in an optical form via one or more optical fibres. More optionally, in the sensor apparatus, the one or more interfacing components are based on a use of Silicon Carbide semiconductor devices.

Optionally, the sensor apparatus is adapted to operate in one of more of: petrochemical facilities, chemical processing facilities, nuclear energy facilities, fermentation tank facilities, food processing facilities, water treatment facilities, waste treatment facilities.

Optionally, the sensor apparatus is arranged to operate such that:
(a) a plurality of beams are susceptible to being used to interrogate sampling points off-axis and on-axis in a cross-section of the region for determining characteristics of the region;
(b) the plurality of beams are employed in a repetitive manner to monitor characteristics of the region;
(c) the transducer arrangement is operable to sense spatially varying attenuation of the received acoustic radiation thereat for determining an occurrence of one or more gas volumes present within the region;
(d) the transducer arrangement is employed for performing time-of-flight measurements for propagation of the acoustic radiation within the region (260) in upstream and downstream directions; and
(e) the transducer arrangement is coupled to a corresponding signal processing arrangement for exciting the transducer arrangement and for processing received signals generate by the transducer arrangement to provide measurement output data representative of phases present within the region.

According to a second aspect, there is provided a method of using sensor apparatus for measuring characteristics of a wall of a structure and/or a medium in contact with the structure, wherein the sensor apparatus includes a transducer arrangement disposed at least partially around a planar or curved surface of a wall of the structure, or disposed over a region of a planar or curved surface of a wall of the structure, characterized in that the method includes:
(a) arranging for the sensor apparatus to include a transducer waveguide including at least one free distal end whereat one or more driver and/or receiver elements are mounted on one or more sides of the at least one free distal end;
(b) operating the transducer arrangement to interrogate the structure to perform at least one of: switching between selected acoustic wave modes present in an acoustic wave propagation, steering an acoustic propagation direction of the acoustic wave propagation; and
(c) operating the one or more driver elements to excite the acoustic wave propagation within the wall of the structure for providing information indicative of properties of the wall and/or material present in a vicinity of the wall which interacts with the acoustic wave propagation.

Optionally, in the method, the transducer arrangement includes a waveguide arrangement which is operable to excite a helical mode acoustic wave propagation in the mechanical structure from the one or more driver elements disposed at one or more ends of the waveguide arrangement.

Optionally, in the method, the one or more driver and/or receiver elements of the transducer waveguide are operable to select one or more specific modes of acoustic radiation propagation by exciting a predominantly through-thickness stress/displacement signature for the one or more specific modes. More optionally, in the method, the one or more driver elements are configurable by selectively exciting them to switch between acoustic radiation modes. More optionally, in the method, the switching between the acoustic radiation modes is achieved by selectively switching between in-phase and out-of-phase excitation of elements on upper and lower faces of one or more distal ends of the transducer waveguide, thereby enabling switching between symmetrical and anti-symmetrical acoustic radiation modes in the transducer waveguide.

Optionally, in the method, the one or more elements have a bandwidth which is sufficient to enable the transducer waveguide to emit acoustic radiation which has a similar dispersion characteristic to a material of the a wall of a structure and/or a medium in contact with the structure.

Optionally, in the method, the one or more driver and/or receiver elements are disposed in a phase array configuration, for enabling an amplitude and/or direction of acoustic modes propagating in the transducer waveguide to be steered.

Optionally, the method includes monitoring a steering angle and/or amplitude of one or more modes excited in the transducer waveguide by using additional one or more sensors attached to the transducer waveguide.

Optionally, the method includes implementing the transducer waveguide as at least of: a sheet of material, a strip, a collar, an annulus, a helical elongate member, a helical strip, a component formed into the wall of the structure.

Optionally, in the method, the one or more receiver elements are implemented optically using one or more Bragg grating sensors.

Optionally, the method includes forming the one or more Bragg grating sensors in one or more silica monomode optical fibres or sapphire monomode optical fibres.

Optionally, in the method, the one or more driver and/or receiver elements are provided with a shielding arrangement for shielding them from thermal and/or ionizing radiation emitted from the structure.

Optionally, in the method, the transducer waveguide is detachably mountable to the structure.

Optionally, in the method, the transducer waveguide has a substantially similar thickness to the wall of the structure, and is fabricated from a material which is substantially similar to that of the wall of the structure. More optionally, in the method, the transducer waveguide is fabricated from at least one of: a metal, a ceramic, a piezoelectric ceramic material, a composite material, a sintered material.

Optionally, the method includes providing the sensor apparatus with a data processing arrangement for generating drive signals to drive the one or more driver elements for selectively interrogating one or more regions adjacent to the wall of the structure, and the data processing arrangement is operable to receive signals from the one or more regions, and to perform tomographic computation upon the information to indentify, in respect of the wall, at least one of: a scale or hydrate deposit on the wall, erosion and/or corrosion of the wall, cracking of the wall. More optionally, in the method, the one or more regions are selectively interrogated by varying an amplitude and/or a relative phase of one or more drive signals applied to the one or more driver elements.

Optionally, the method includes provided the sensor apparatus with further one or more environmental sensors disposed in a region between an outer surface of the wall of the structure and a cladding of the structure, wherein the one or more environmental sensors are disposed remotely in respect of the transducer waveguide and are operable to receive acoustic radiation coupled along the wall of the structure to the one or more environmental sensors. More optionally, in the method, the one or more environmental sensors are operable measure chemical parameters relating to at least one of: liquid water, humidity, salinity, pH and electrical conductivity. More optionally, in the method, the transducer waveguide and the one or more environmental sensors employ a common optical fibre with sensors formed therealong for sensing purposes.

Optionally, in the method, at least one transducer waveguide of the transducer arrangement includes a first end thereof and a second end thereof, wherein an array of transducer elements is disposed at the first end and are individually excitable in a phase-array manner for steering the one or more beams within the region.

Optionally, in the method, the at least one waveguide of the transducer arrangement includes one or more transducer elements disposed at the second end for monitoring integrity of operation of the waveguide and/or for enabling a temperature compensation to be applied by a signal processing arrangement for operation of the waveguide.

Optionally, in the method, the transducer arrangement includes a spatially distributed array of sensors disposed on an external surface of the wall for receiving acoustic radiation coupled through the wall thereto.

Optionally, in the method, the spatially distributed array of sensors is interspersed between waveguides of the transducer arrangement for generating the one or more beams.

More optionally, in the method, the spatially distributed array of sensors is implemented using a plurality of Bragg grating filter sensors distributed along one or more optical fibres, wherein the Bragg filter sensors are optically interrogated in operation via optical radiation guided through the one or more optical fibres and selectively reflected and/or transmitted at the Bragg grating filter sensors (FBG).

Optionally, in the method, the transducer arrangement includes one or more interfacing components which enabled the transducer arrangement to be excited from one or more optical signals conveyed via one or more optical fibres coupled to the sensor apparatus and/or to output its received acoustic radiation signals via the wall in an optical form via one or more optical fibres. More optionally, in the method, the one or more interfacing components are based on a use of Silicon Carbide semiconductor devices.

Optionally, in the method, the sensor apparatus is adapted to operate in one of more of: petrochemical facilities, chemical processing facilities, nuclear energy facilities, fermentation tank facilities, food processing facilities, water treatment facilities, waste treatment facilities.

Optionally, the method includes arranging for sensor apparatus to operate such that:
(a) a plurality of beams are arranged to interrogate sampling points off-axis and on-axis in a cross-section of the region for determining characteristics of the region;
(b) the plurality of beams are employed in a repetitive manner to monitor temporal fluctuations in the region;
(c) the transducer arrangement is operable to sense spatially varying attenuation of the received acoustic radiation thereat for determining an occurrence of one or more gas volumes present within the region;
(d) the transducer arrangement is employed for performing time-of-flight measurements for propagation of the acoustic radiation within the region in upstream and downstream directions; and
(e) the transducer arrangement is coupled to a corresponding signal processing arrangement for exciting the transducer arrangement and for processing received signals generate by the transducer arrangement to provide measurement output data representative of an indication of phases present in the region (gas fraction).

According to a third aspect, there is provided a computer program product comprising a non-transitory computer-readable data storage medium having computer-readable instructions stored thereon, the computer-readable instructions being executable by a computerized device comprising processing hardware to execute the method of the second aspect.

It will be appreciated that features of the invention are susceptible to being combined in various combinations without departing from the scope of the invention as defined by the appended claims.

DESCRIPTION OF THE DIAGRAMS

Embodiments of the present disclosure will now be described, by way of example only, with reference to the following diagrams wherein.

Figure 3:
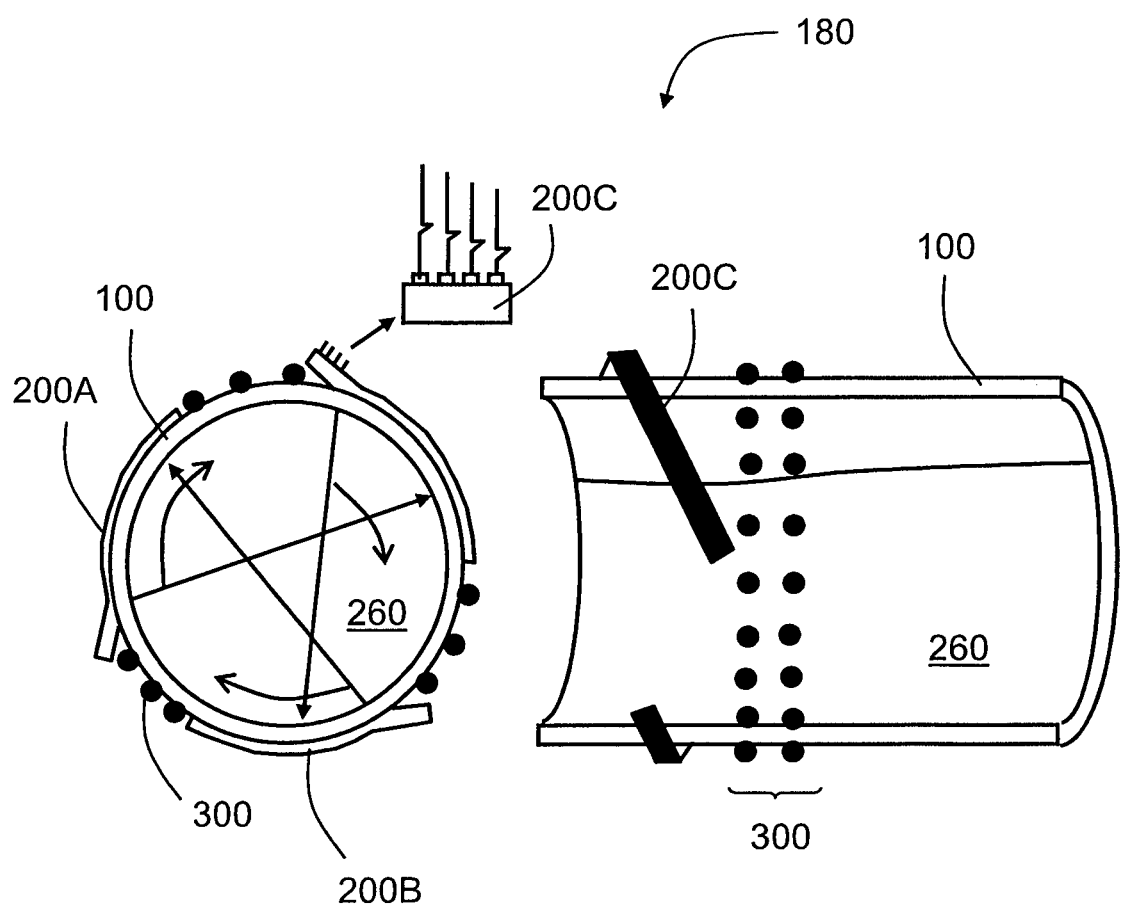
FIG. 3 is a schematic cross-section illustration of a conduit, wherein a radial disposition of transducer arrangements for measuring characteristics of the conduit is shown.
Figure 10:
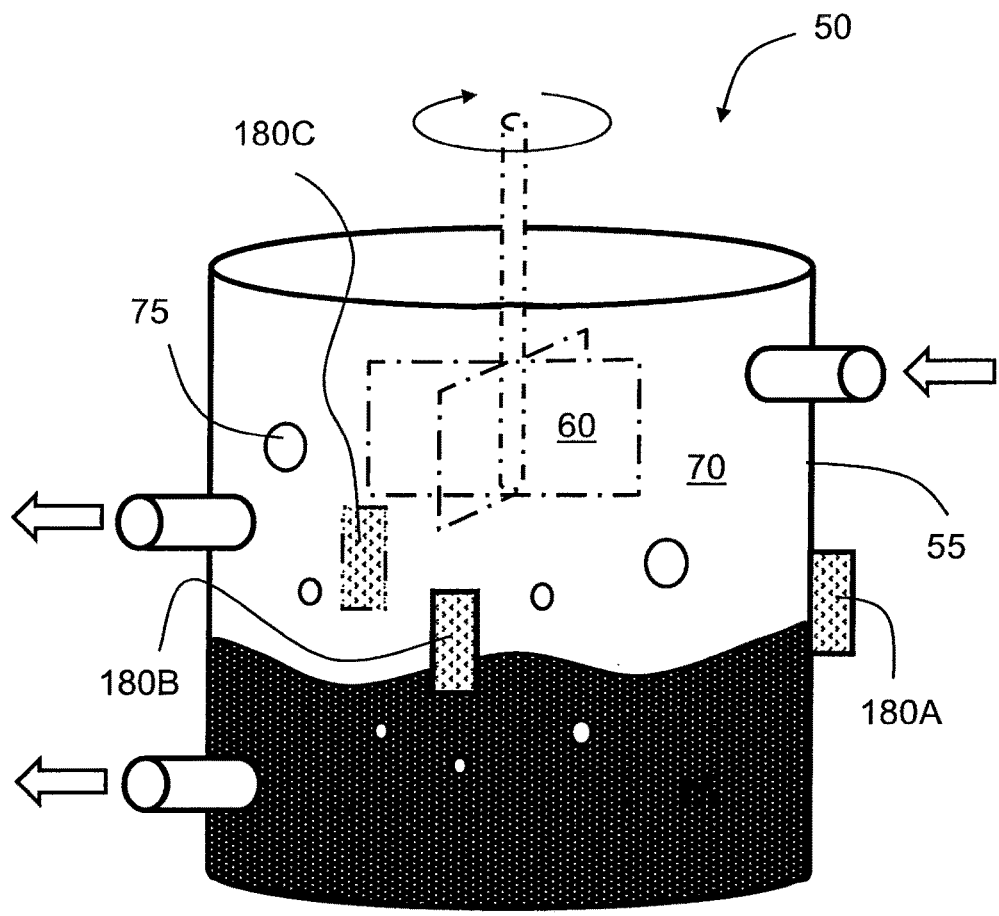
Figure 11:
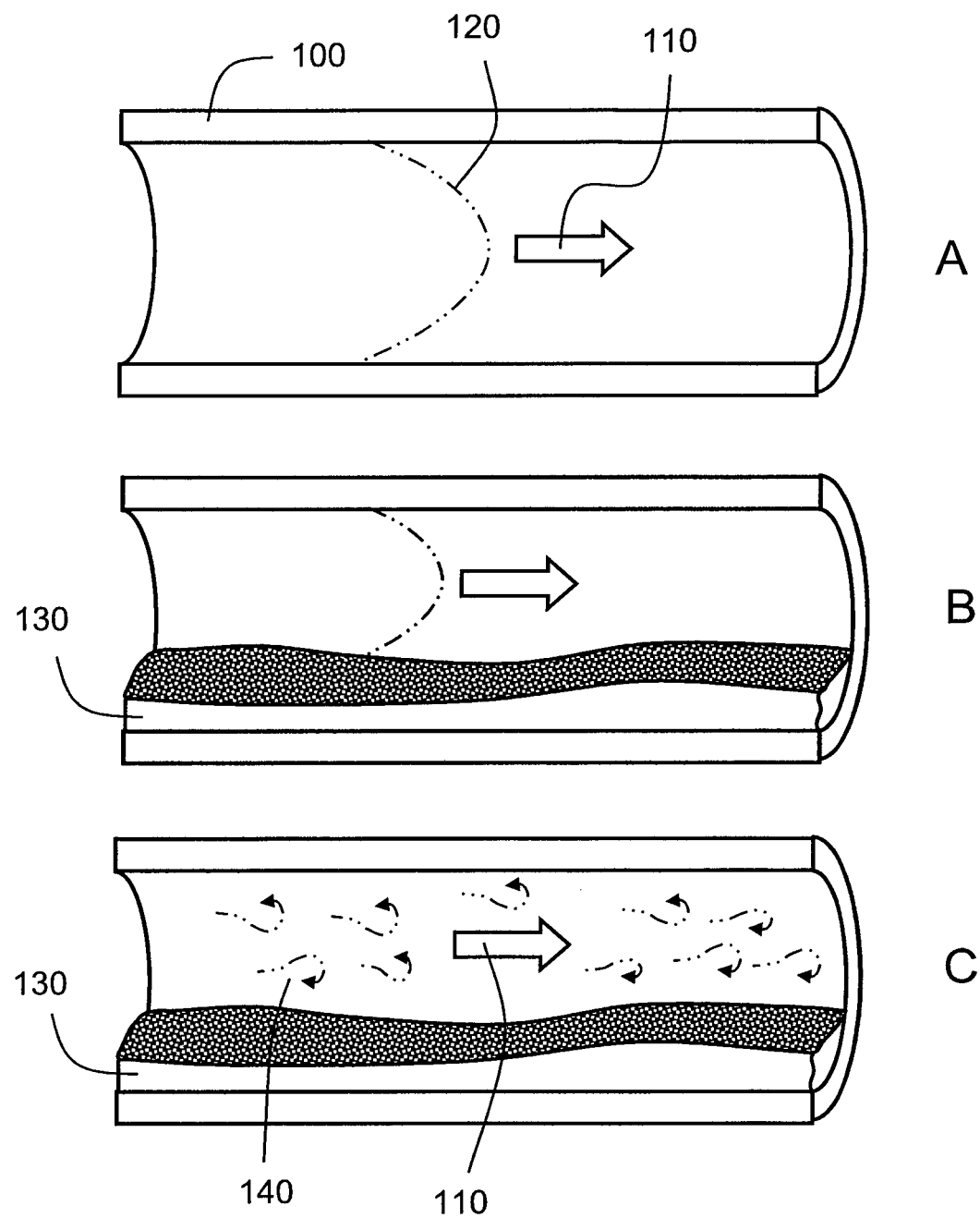
Figure 12:
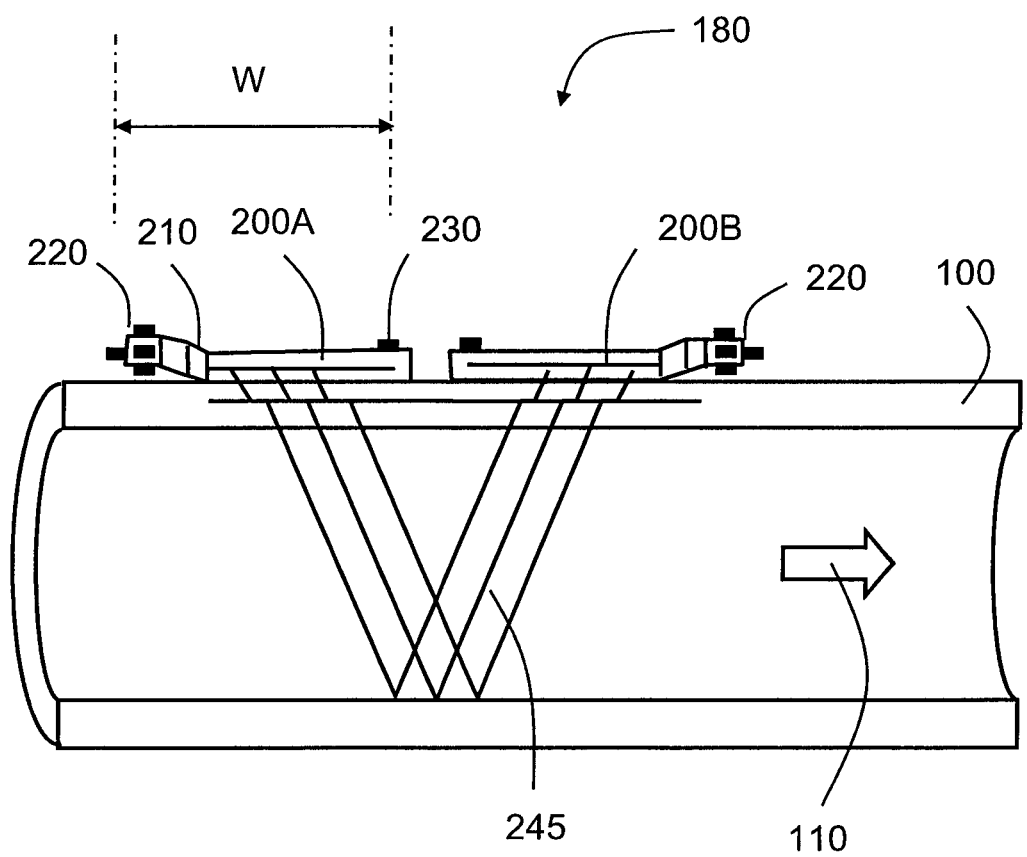
Figure 13:
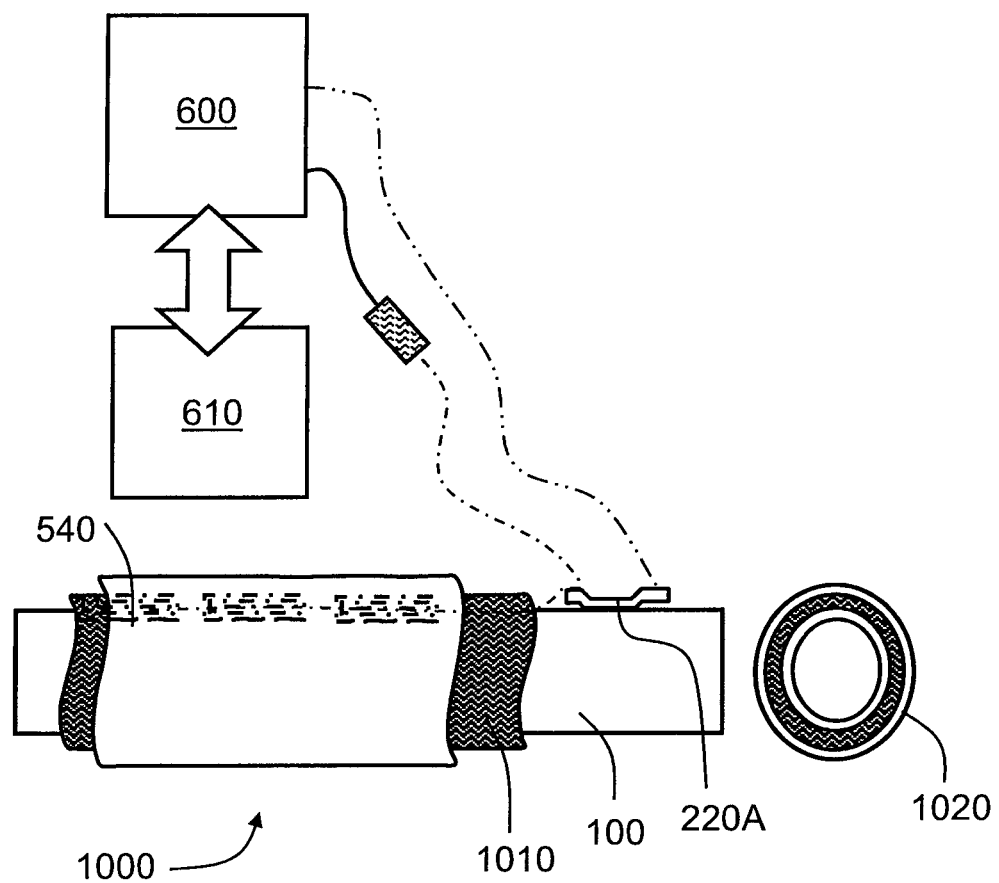

FIG. 10 is an illustration of a processing tank including one or more inlets and one or more outlets, wherein the process tank potentially includes a multiphase mixture, and wherein the processing tank relates, for example, to one or more of: a chemical processing plant, a bio-fermentation facility, a nuclear waste separation facility, but limited thereto FIG. 11 is a schematic illustration of spatially inhomogeneous phases present within a conduit;

FIG. 12 is an illustration of the conduit or pipe of FIG. 3, wherein upstream and downstream measurement positions are shown;

FIG. 13 is an illustration of a manner in which transducers are mounted to the conduit of FIG. 3 for structural measuring purposes, in a manner as generally described in the published international PCT patent document WO2014/098613A1 ("Sensor System for Corrosion Monitoring", Applicant—TeCom AS), as aforementioned, hereby incorporated by reference.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS

In overview, a sensor apparatus pursuant to the present disclosure beneficially employs "CMR Guided Wave" technology as described in Norwegian patent NO331687 and corresponding GB patent GB2479115B, PCT patent application WO2011/078691A2 and U.S. Pat. No. 8,141,434B2, which are hereby incorporated by reference. Moreover, the sensor apparatus is susceptible to being employed, for example, to implementing a sensor apparatus for measuring structural characteristics of a conduit, for example by way of performing a differential measurement are described in an international PCT patent application PCT/NO2010/000480 (Tecom AS and Christian Michelsen Research AS), the contents of which are hereby incorporated by reference.

In the following description, the term "acoustic" is to be construed broadly to include any acoustic signals, for example in a frequency range of 100 Hz to 50 MHz, more optionally 300 Hz to 50 MHz, and yet more optionally in a range of 500 Hz to 100 kHz, for example aforesaid ultrasonic radiation.

Referring next to FIG. 11, there is shown an example of a flow, denoted by an arrow 110, through a vessel or conduit denoted by 100. In a situation A, the flow 110 is laminar, namely non-turbulent, wherein a spatial velocity of the flow 110 decreases as a function of a radial distance from a central elongate axis of the conduit 100. A lower flow velocity occurring locally at an inside wall of the conduit 100 can, for example, give rise to deposition, for example formation of scale or hydrate deposit on the inside wall, over a prolonged period of operation; such deposits can potentially eventually cause a blockage of the conduit 100, resulting in a back-pressure being established which could, for example, eventually risk rupturing the conduit 100. The flow 110 can be a complex flow, for example spatially substantially homogeneous, or spatially inhomogeneous as illustrated in situation B, wherein a spatial region 130 has a different composition to a remainder of the flow 110 within the conduit 100. However, when the flow 110 exceeds its Reynolds number $R_e$, see Equation 1 (Eq. 1) below, turbulent flow occurs, resulting potentially in vortices 140 and other instabilities, wherein a broadened spectrum of flow velocities within the conduit 100 occurs; turbulent flows can potentially, for example, cause the conduit 100 to be subjected to oscillatory stresses that can eventually cause microcracks to form in the wall of the conduit 100, which risk the conduit 100 rupturing, especially if the conduit 100 is subsequently subject to an aforementioned back-pressure. In certain circumstances, the flow 110 potentially ceases, resulting in a precipitation of sediment, for example scale and/or hydrate, within the conduit 100, which, for example, may result in the conduit 100 becoming blocked, as aforementioned. Similar considerations pertain mutatis mutandis to a vessel or container in which a multiphase mixture is contained, for example in a chemical processing vessel, a biological digester, a food waste processing apparatus, filtration tanks for a nuclear isotope separation facility, and so forth.

For coping with characterizing situations similar to chose illustrated in FIG. 11, there is provided a sensor apparatus pursuant to the present disclosure, as will be elucidated in greater detail below. The sensor apparatus pursuant to the present disclosure is beneficially susceptible to being employed to implement following measurement regimes, for example when used as a part of an instrumentation system:

(i) for generating directed short pulses, for example a train of short pulses, for example a time-gated train of short pulses, of acoustic radiation for monitoring structural characteristics of a mechanical structure, for example a planar structure, a vessel, a curved structure such as an aircraft wing or rotor of a renewable energy system, a hollow structure such as a vessel or conduit, as well as detecting for precipitation or scale build-up in respect of the mechanical structure;

(ii) for generating pure mode leaky Lamb waves for monitoring liquid in a gas flow within a conduit or vessel, for example as illustrated in FIG. 3.

Figure 1A:
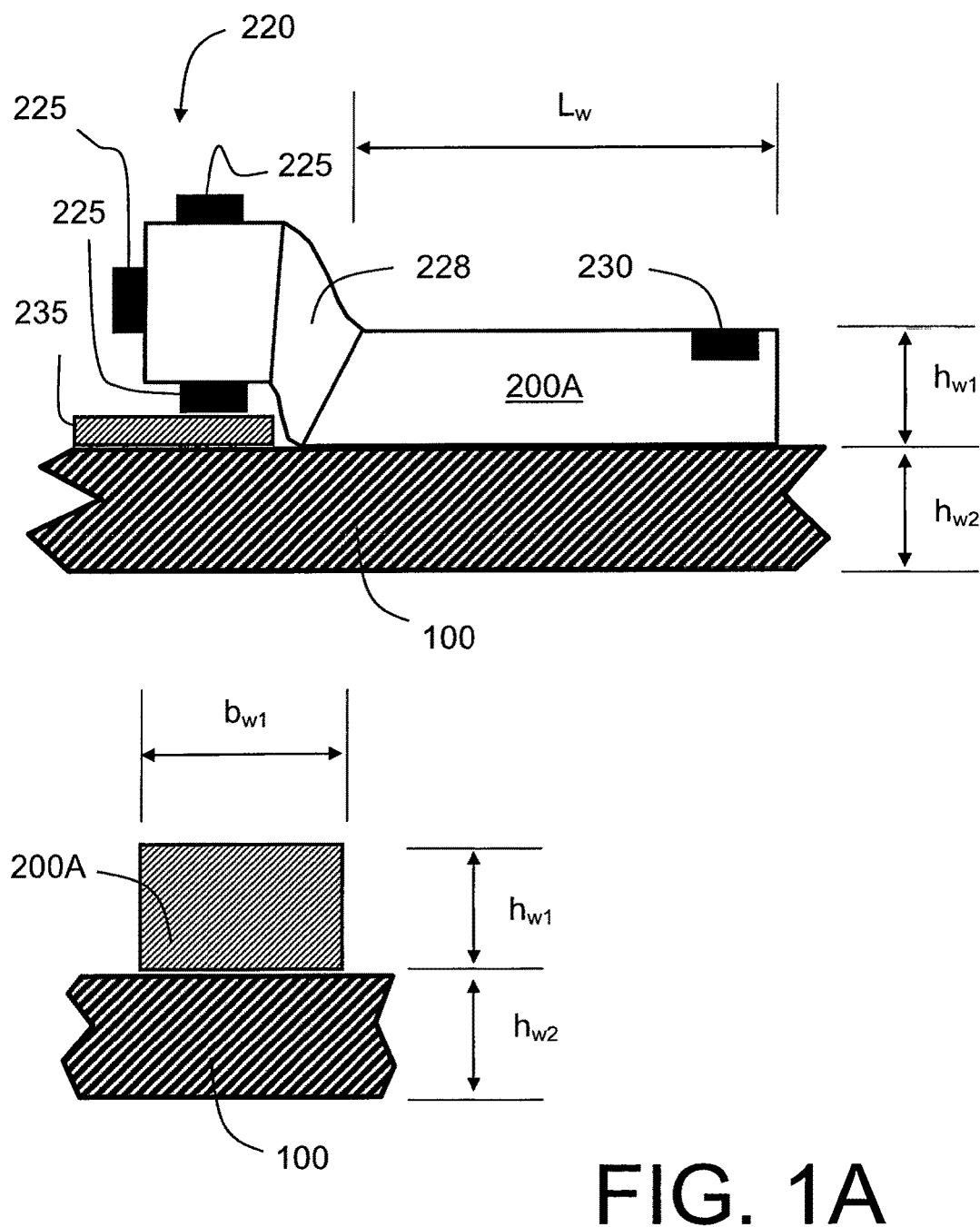
FIG. 1A, FIG. 1B, FIG. 1C, FIG. 1D and FIG. 1E are schematic illustrations of transducer arrangements that are employed in embodiments of a sensor apparatus pursuant to the present disclosure.
Figure 1B:
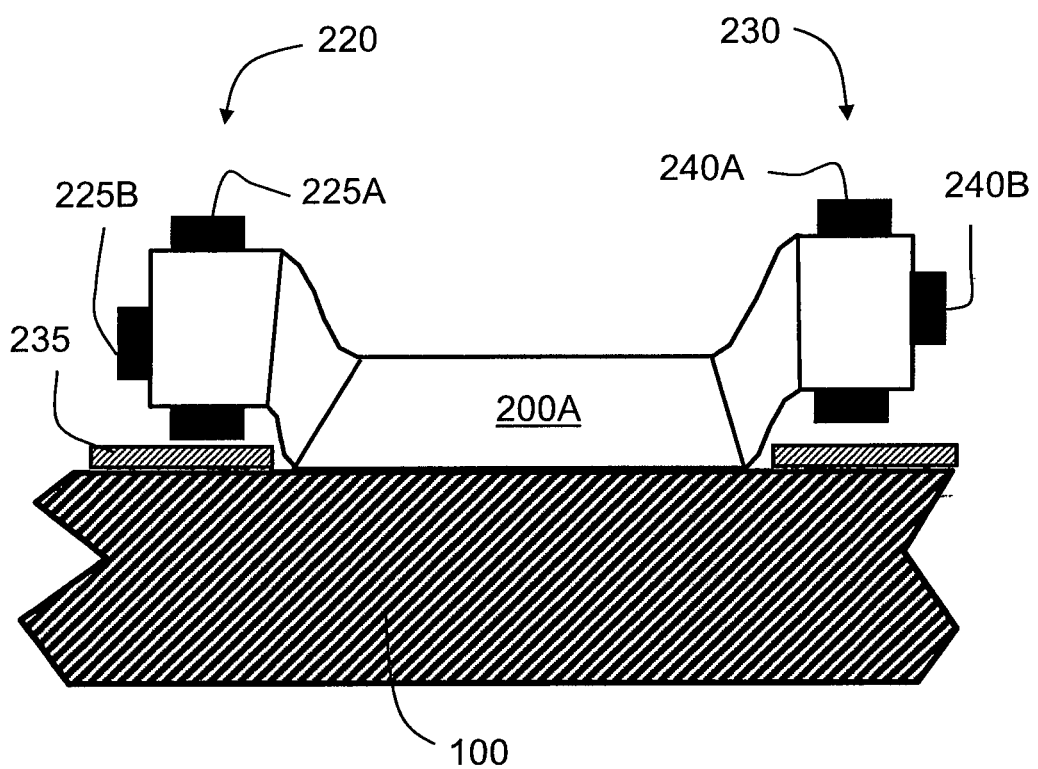
Figure 1C:
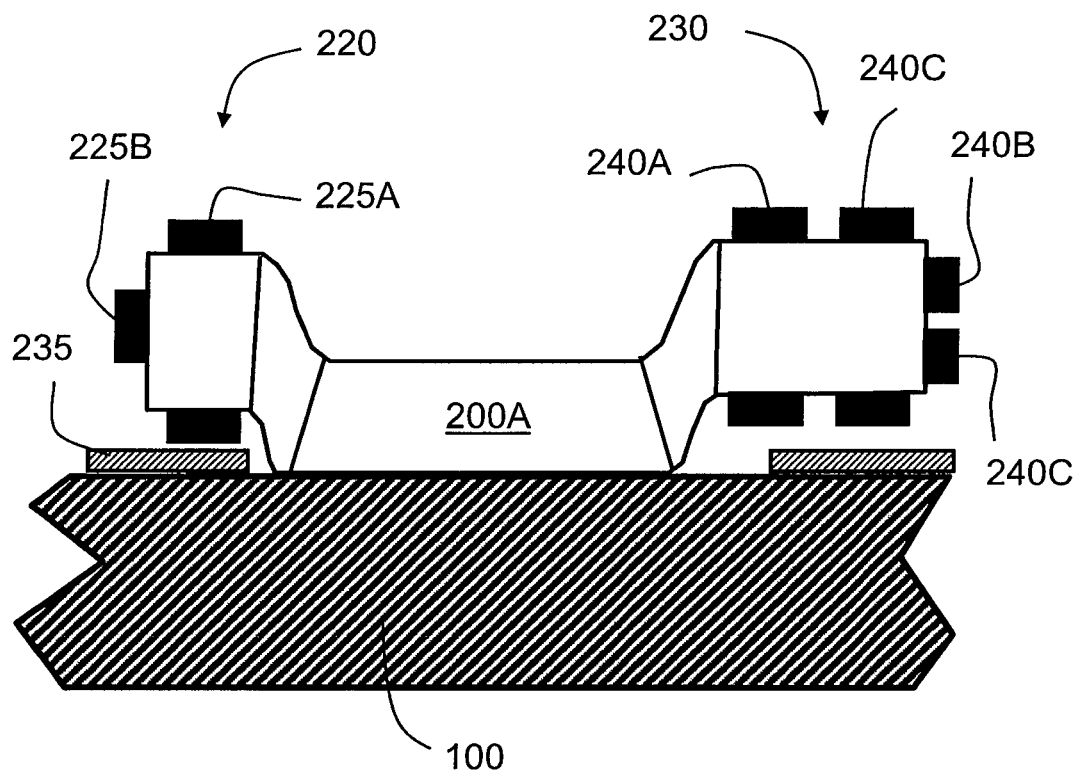
Figure 1D:
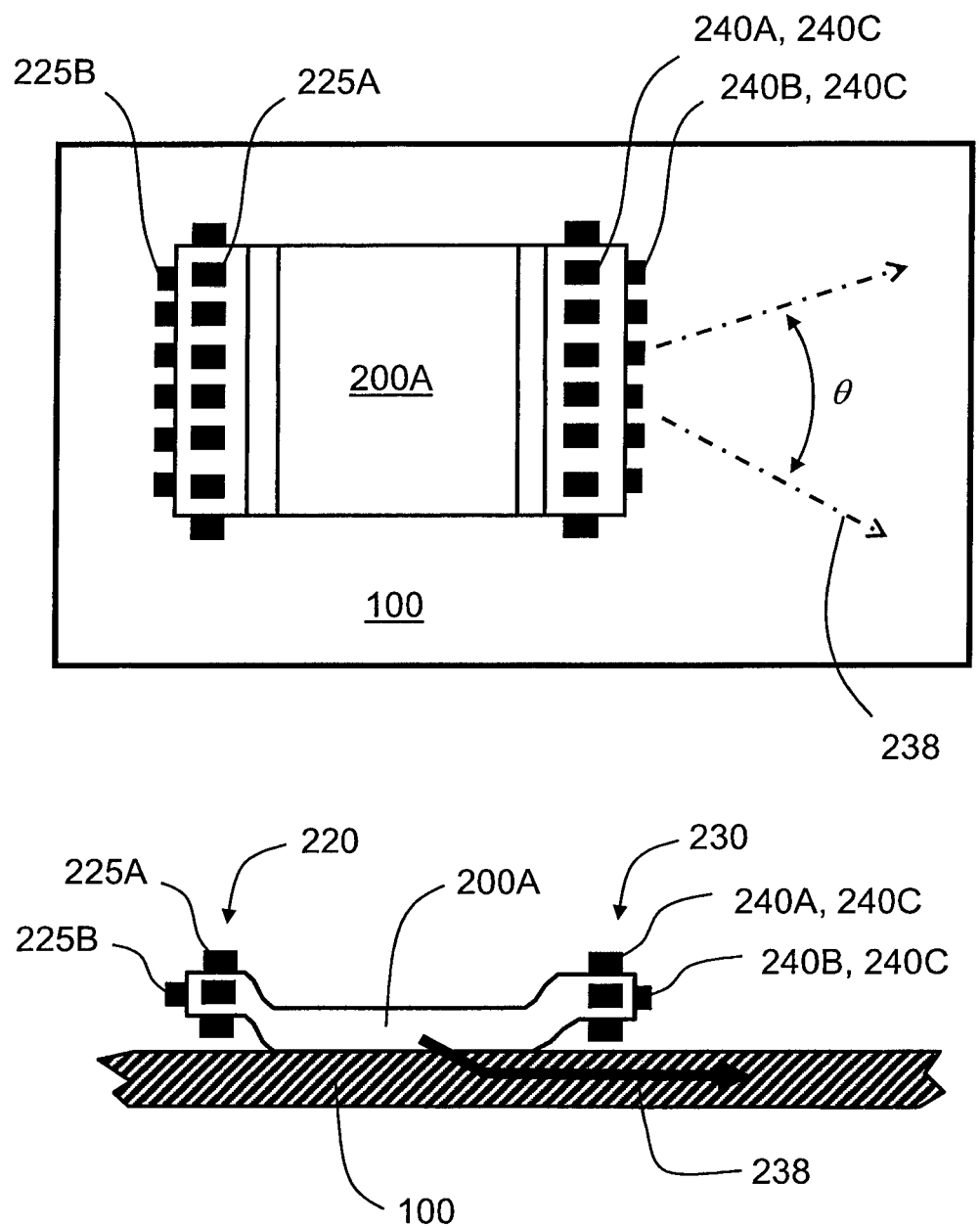
Figure 4:
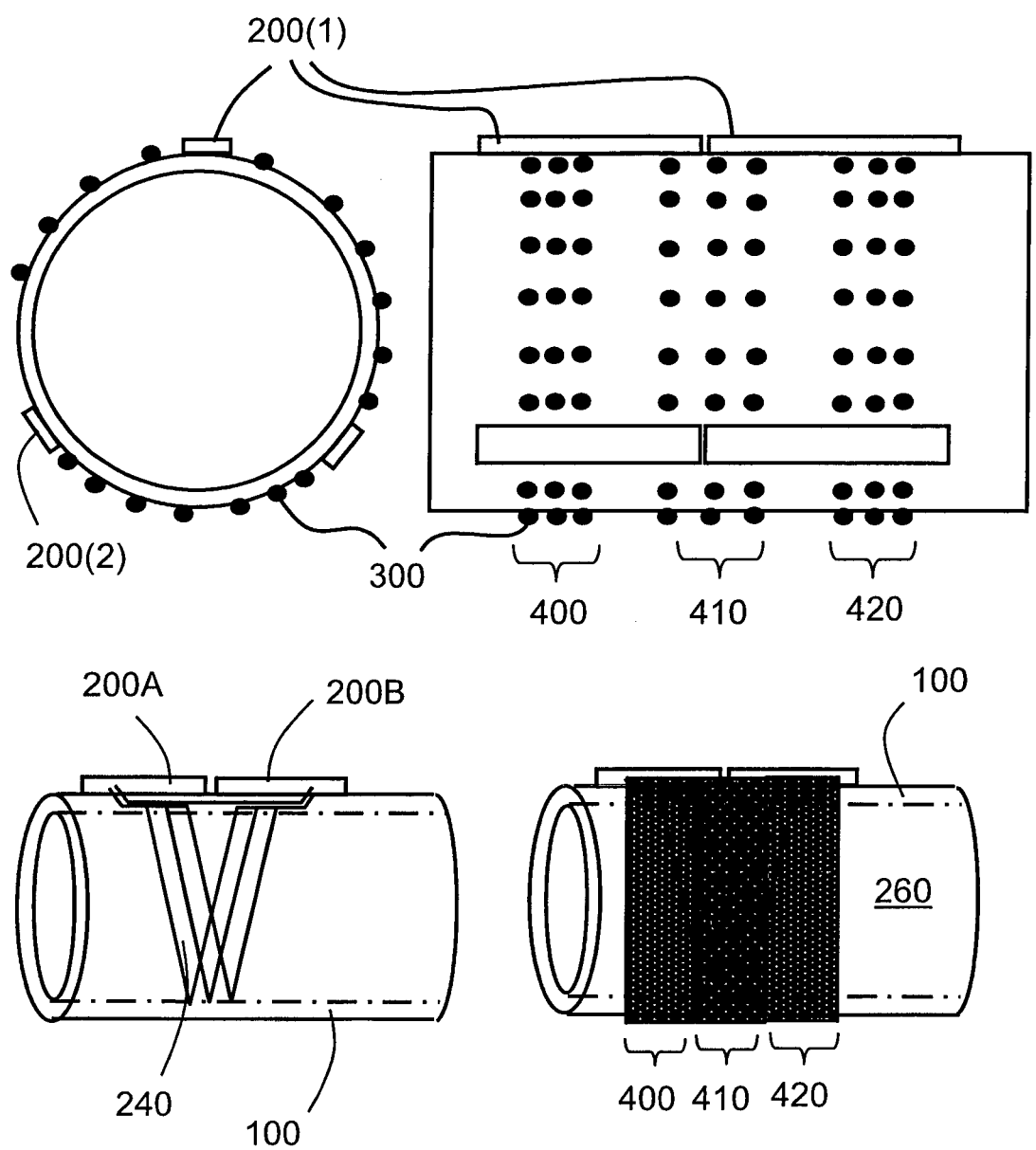
FIG. 4 is an illustration of the conduit of FIG. 3, wherein an arrangement for measuring within the conduit is shown.
Figure 7:
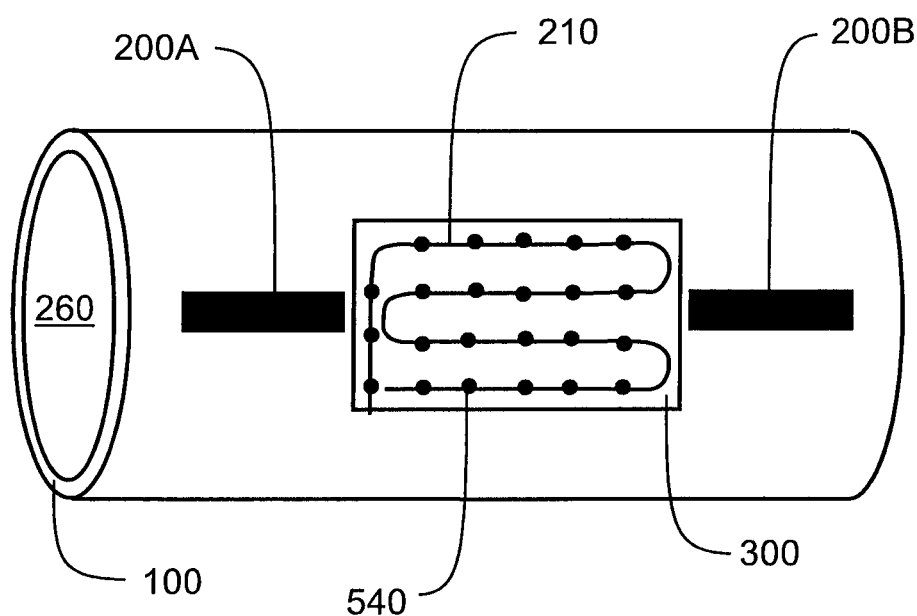
FIG. 7 is an illustration of an arrangement for emitting transducers and receiving transducers for measuring flow within the conduit or pipe of FIG. 3.

Referring next to FIG. 3, together with FIG. 1A, FIG. 1B, FIG. 1C, FIG. 1D and FIG. 1E there is shown a part of a sensor apparatus indicated generally by 180; although the sensor apparatus 180 is shown applied to a curved surface, it will be appreciated that the apparatus 180 can be arranged to monitor structural characteristics of a planar structure, for example a sheet of material by employing waveguides having a linear elongate format rather than a helical format, for example as illustrated in the FIG. 1D wherein a beam 238 of relatively pure-mode acoustic radiation is generated which is steerable over an range of angles θ. The sensor apparatus 180 includes an arrangement of transducers for implementing a measuring instrument pursuant to the present disclosure. The arrangement of transducers includes a first transducer including an elongate waveguide 200A having a length W measuring from a cluster or array of acoustic elements indicated generally by 220, wherein each element is denoted by 225, disposed at a first end of the waveguide 200A, via a coupling neck region 218, to a monitoring element 230 disposed at a second end of the waveguide 200A as illustrated. The arrangement of transducers optionally further includes a second elongate waveguide 200B disposed in a mirror orientation to the first elongate waveguide 200B, in a manner as illustrated in FIG. 4 and in FIG. 7; in FIG. 4 and FIG. 7, the waveguide 200B is optionally implemented in an elongate helical manner as illustrated in FIG. 3. Sides of the waveguides 200A, 200B are attached to an external surface of the conduit 100 for coupling acoustic radiation into a wall of the conduit 100 and therefrom, via Lamb wave or similar modes of propagation, to an interior region of the conduit 100 in which the flow 110 occurs in operation, and where scale deposition and/or wall thinning due to corrosion or erosion can potentially occur. The acoustic radiation is optionally selectively in a form of one or more broad acoustic radiation beams, and/or one or more narrow acoustic radiation beams. Optionally, when the cluster or array of acoustic elements 220 is implemented as a form of phased array, driven with signals which are mutually similar, but mutually temporally shifted or phase shifted, so as to control precisely a form of acoustic mode established in the waveguides 200A, 200B:

(a) for steering a corresponding acoustic radiation beam emitted in operation from the wall of the conduit 100 in a spatial vicinity of the waveguides 200A, 200B; or
(b) for steering a direction of greatest sensitivity when receiving acoustic radiation in operation at the wall of the conduit 100 in a spatial vicinity of the waveguides 200A, 200B.

Referring to FIG. 10, the sensor apparatus 180 is susceptible to being used to monitor an interior volume of a tank 50, wherein the tank 50 is optionally provided with a stirrer 60 for agitating an interior volume of the tank 50. The tank 50 is optionally a petrochemicals processing tank, a fermentation tank, a separation tank, an intermediate nuclear waste tank, a water treatment tank, but not limited thereto. The tank 50 has peripheral wall to which three sensor apparatus 180A, 180B, 180C are mounted, as illustrated. In operation, the tank has an inner volume 70 which is interrogated by the sensor apparatus 180A, 180B, 180C. The inner volume 70 is susceptible to containing a complex mixture, for example a region 75 of solid deposit, regions of gas bubbles 75 and various types of liquids. The tank 50 represents a complex environment which is potentially static, alternative flowing, and potential with laminar or turbulent motion. For an operator of the tank 50, it is desirable to monitor what is happening within the tank 50 when materials are fed to the tank 50, and removed from the tank 50, via one or more connection ducts.

The waveguides 200A, 200B of the sensor apparatus 180 are beneficially fabricated from a material which provides an environment in which acoustic radiation is able to propagate, with an acoustic wave impedance which is considerable greater than a material cladding the waveguides 200A, 200B, and which is at least partially matched to an acoustic wave impedance of a material employed for fabricating the wall of the conduit 100. Suitable materials for the wave guides 200A, 200B optionally include at least one of:

(a) a metal, for example stainless steel, Hastelloy-N, Copper, Nickel, metal alloy;
(b) a ceramic material, for example Silicon Nitride ceramic, Silicon Carbide ceramic, glass ceramic;
(c) a polymeric plastics material, for example PEEK, a glass, silica glass;
(d) a composite material, for example a silicon carbine sintered ceramic, a piezoelectric material such as lead zirconate titanate,
but not limited thereto.

Optionally, the waveguides 200A, 200B are made to a size which is a function of an acoustic radiation wavelength of acoustic radiation which they are required to propagate. The length W of the waveguides 200A, 200B is beneficially a plurality of wavelengths long. Moreover, the waveguides 200A, 200B have a width and height which only supports acoustic radiation of wavelengths employed to interrogate the region of volume 260. Optionally, the sensor apparatus 180 employs a plurality of different types of waveguides 200A, 200B which are excitable at mutually substantially different frequencies, for example to obtain more information regarding a nature of multiphase mixture present in the region or volume 260. Beneficially, the waveguides 200A, 200B, 200C have a height thickness above a surface onto which they are mounted in operation which is substantially equal to a thickness of a wall or plate, wherein the mounting surface is a surface of the wall or plate. By "substantially similar" is meant in a range of 80% to 120%, more optionally in a range of 95% to 105%. Moreover, the waveguides 200A, 200B, 200C are beneficially manufactured from a material which is similar to that of the wall or plate to which they are mounted in operation. Optionally, the waveguides 200A, 200B, 200C are an integral part of their associated wall or plate, for example machined from a unitary material. Beneficially, the waveguides 200A, 200B, 200C have substantially similar mode dispersion properties to that of a wall or surface onto which they are mounted in operation; "substantially", for example, relates to in a range of 90% to 110% similar.

In operation, with reference to FIG. 3 and FIG. 4, measurements are made, for example, with the acoustic radiation 240 projected in upstream and downstream directions relative to the flow 110, and a differential computation is performed on received phase shifted, namely Doppler-shifted, acoustic radiation, thereby removing many sources of measurement error in the sensor apparatus 180. The monitoring elements 230 are beneficially employed to monitor acoustic radiation coupled from the cluster of acoustic elements 220 to the waveguide 200A, thereby enabling correction of element characteristics to be compensated, for example changes in piezo-electric coupling coefficient of the elements of the cluster as a function of operating temperature and/or time; mutatis mutandis similar consideration pertain to the waveguides 200B, 200C. For example, the piezo-electric elements have a coupling coefficient which slowly reduces as a function of time, for example as a result of element depolarization. When performing such measurements, it is feasible to determine whether or not scale or hydrate build-up is occurring in the conduit 100, because an excessive flow velocity potentially indicates a constriction inside the conduit 100 due to scale and/or hydrate build-up. Likewise, a reduced flow rate is potentially indicative of the conduit 100 having a larger internal diameter, for example as a result of erosion or corrosion.

Apart from directing beams of acoustic radiation through an interior volume of the conduit 100, the waveguides 200A, 200B, 200C are also operable to launch Lamb waves and/or Rayleigh waves into the wall of the conduit 100, wherein such beams propagate.

Optionally, the cluster of acoustic elements 220 are provided with electrical drive signals, for example wherein the acoustic elements 220 are implemented as piezo-electric transducers, for example fabricated from polarized lead zirconate titanate. Alternatively, or additionally, the cluster of acoustic elements 220 are provided with drive signals conveyed via one or more optical fibres, wherein each acoustic element 225 includes locally thereto an optical-to-electric converter (not shown), for example implemented as a stack of photodiodes, so that optical signals provided via one or more optical fibres are converted to electrical signals for exciting the acoustic element 225, see FIG. 1A for example. Such an arrangement is highly desirable in environments where intrinsic safety is required, for example in hazardous petrochemical facilities with flammable gases such as methane being present; the stack of photodiodes is beneficially, for example, encapsulated to ensure that it is intrinsically safe. Moreover, the stack of photodiodes is optionally fabricated from materials, such as Silicon Carbide, which are capable of surviving high levels of ambient ionizing radiation, for example when the sensor apparatus 180 is employed for nuclear plant, for decommissioning nuclear facilities such as Fukushima Dai'ichi, and similar. By such an approach, the sensor apparatus 180 is potentially useable for monitoring flows of cooling water to and from nuclear reactor cores where meltdown has occurred or a China syndrome situation has arisen. Fibre optic components and Silicon Carbide semiconductor devices are capable of operating at elevated temperatures which would be damaging to conventional Silicon-based semiconductor devices, for example at temperatures of 250° C. or more. Optionally, silica monomode optical fibre is employed in most situations, and sapphire monomode fibre is employed in environments wherein high fluxes of ionizing radiation are likely to be encountered.

Optionally, when the acoustic elements 225 are employed to receive acoustic radiation and generate corresponding signals, each such element 225 is provided with a preamplifier (not shown) which is beneficially energized via optical radiation conveyed via one or more optical fibres to a photodiode stack in close spatial proximity to the element 225 and coupled to the preamplifier; moreover, the preamplifier beneficially provides a modulating signal to a light source, for example via a current modulator providing a drive current to a laser diode (not shown), or via a Mach-Zehnder optical modulator provided with a light signal from a laser diode. The modulated light signal is beneficially conveyed back via one or more optical fibres to a remote monitoring location. Such an implementation, especially when component parts involved are encapsulated, is susceptible to being intrinsically safe in aforesaid hazardous petrochemical environments, and is capable of being employed for prolonged periods in sub-sea installations. On account of a compact manner in which the acoustic elements 225 may be implemented, they are also suitable for use in hazardous radioactive environments, for example when decommissioning nuclear plant and/or in nuclear waste treatment facilities.

The acoustic elements 225 are each beneficially implemented as a stack of piezoelectric plates which are electrically connected in parallel so that relatively small potentially are required to drive the acoustic elements 225. The acoustic elements 225 are beneficially fabricated from various compositions including lead zirconate titanate (PZT) as aforementioned. Alternative, piezoelectric plastics materials can alternatively be utilized, for example in situations where the apparatus 180 is employed in biological systems where a risk of any toxic materials must be avoided.

The elongate waveguides 200A, 200B provide transducers that are superior to known acoustic transducers employing wedge-shaped acoustic coupling elements. Such superiority pertains, for example, to improved guided wave properties and better beam formation of the acoustic radiation 240, for example arising as ultrasonic radiation. Thus, the elongate waveguides 200A, 200B are operable to provide improved directing and shaping of selected acoustic mode transmission within the conduit 100, and within the wall of the conduit 100 for enabling its structural characteristics to be determined, for example onset of embrittlement, cracking, thinning due to erosion or corrosion, deposition of scale or hydrate, and so forth. Moreover, the elongate waveguides 200A, 200B are operable to provide improved suppression of acoustic modes which have not been selected for use in the sensor apparatus 180, thereby enhancing a measurement signal-to-noise ratio of the sensor apparatus 180. For example, the waveguides 200A, 200B, 200C are beneficially used to excite Lamb waves into the wall of the conduit 100, wherein the Lamb waves are efficiently coupled to corresponding acoustic detectors, for example implemented with Bragg grating sensors mounted onto the wall of the conduit 100 or by use of the waveguides 200A, 200B, 200C to receive radiation. Embrittlement, cracks, scale deposits, hydrate deposits, erosion areas, namely structural defects, are operable to cause mode dispersion within the wall of the conduit 100, so unexpected attenuation of Lamb waves and/or increased received signals pertaining to dispersion modes is potentially indicative of the structural defects.

In comparison to known wedge-coupling-element technology, the elongate waveguides 200A, 200B, additionally results in less signal drift caused by thermal wedge material expansion and contraction, as well as increased transducer foot-print area onto the external surface of the conduit 100, namely more acoustic radiation coupled into the conduit 100 and its associated wall. Additionally, the waveguides 200A, 200B have an extended physical length, in comparison to known wedge-design transducers, which enables additional acoustic pickup, for performing following functions:

(i) acoustic energy is coupled into a sensing direction of a correspondingly shaped receiving transducer, thereby improving measurement signal-to-noise performance of the apparatus 180; and (ii) acoustic energy is focused in a direction and shape of a receiving array of sensors, for example Bragg-grating sensors, as will be described in greater detail later Spatial free ends of the waveguides 200A, 200B are provided with the one or more monitoring elements 230, as shown in FIG. 1A, FIG. 1B, FIG. 1C, FIG. 1D and FIG. 1E, which are beneficially employed in a feedback manner to control drive signals to the cluster of acoustic elements 225 to optimize their operation, for example for achieving an enhanced measurement signal-to-noise ratio. Optionally, the cluster of elements 225 are installed in a same plane or at different angles along x-, y- and z-axes, and controlled individually with respect of signal wave phase, namely in a manner of a phased array:

(i) for achieving an optimal operating signal-to-noise ratio;
(ii) for controlling acoustic transmission angle excitation in respect of the conduit 100, in respect of acoustic wave propagation within the wall of the conduit 100, and one or more phases present within the conduit 100; and
(iii) for achieving sequential transmission angles for the acoustic radiation 245, see FIG. 12, as well as signal shape and/or signal quality for exciting various types of signals on demand, for example a given number of pulses X in a first given transmission angle for the radiation 245, followed by a given number of pulses Y in a second given transmission angle for the radiation, then returning to the given number of pulses X in the first given transmission angle, and so forth; there is thereby obtained two sets of measurements representing mutually different fluid properties by employing only one set of transducers, as illustrated in FIG. 12.

The sensor apparatus 180 of the disclosure described above provides numerous benefits in comparison to known flow meters. In a known ultrasonic "clamp-on" type flow meter, namely single-phase meters, acoustic radiation is transmitted in a radial manner in a cross-section of a given conduit, and at an angle determined by a wedge-element geometry employed in the known flow meters. As a result, measurement occurs primarily at a central region of the given conduit, such that, when the given pipe is gas-filled at its centre and a remainder of the pipe is liquid-filled, reflecting of acoustic radiation is severely affected, potentially resulting an no flow measurement being possible to obtain.

Figure 6:
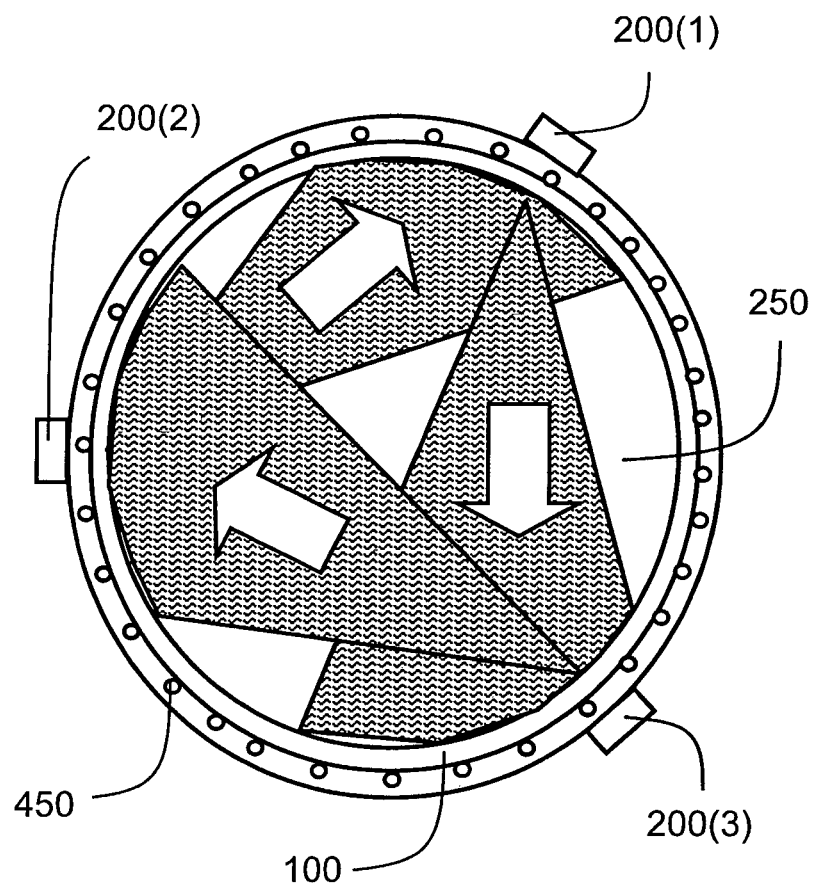
FIG. 6 is an illustration of the conduit of FIG. 3, wherein an alternative arrangement for measuring within the conduit is shown.

Referring to FIG. 6, a transverse cross-section illustration of the conduit 100 is shown, wherein the sensor apparatus 180 is implemented to include three sets of waveguides 200(1), 200(2), 200(3). These three sets of waveguides 200(1), 200(2), 200(3) are disposed at 120° intervals around an external circumference of the conduit 100; each set includes two transducers, for example as illustrated in FIG. 4. The conduit 100 encloses a volume 260 in which the flow 110 occurs in operation. The three waveguides 200(1), 200(2), 200(3) in temporal sequence are operable to emit beams, for example denoted by 250, of acoustic radiation, for example ultrasonic radiation but not limited thereto, into the volume 260 for use in characterizing the flow 110. The three waveguides 200(1), 200(2), 200(3) are also operable to launch relatively pure selectively-steerable helical-mode waves, for example propagating as Lamb waves, into the wall of the conduit 100 for structurally characterizing the wall; additionally, or alternatively, higher frequency Rayleigh waves are launched into the wall. Attenuation of Rayleigh wave propagation and/or helical mode propagation within the wall provides a measure of potential occurrence of structural defects, as aforementioned, in the wall. Moreover, mode scattering from helical mode propagation or Rayleigh wave propagation in the wall as a function of time is also potentially indicative of gradual development of structural defects.

The sensor apparatus 180 illustrated in FIG. 3, and FIG. 4, with its associated signal processing arrangement, is capable of measuring characteristics of the flow 110 in both laminar flow conditions and turbulent flow conditions, for example by suitably reconfiguring itself, as will be described in more detail later. An onset of turbulence occurs in the flow 110 when its Reynolds number $R_e$ exceeds a threshold value, as will next be elucidated. The Reynolds number $R_e$ is susceptible to being computed from Equation 1 (Eq. 1):

$$R_e = \frac{\rho V D}{\mu} \quad \text{Eq. 1}$$

wherein
$R_e$=Reynolds number, wherein a value $R_e<2300$ corresponds to a laminar flow, a value $2300<R_e<4000$ corresponds to a transitional flow, and a value $R_e>4000$ corresponds to a turbulent flow;
V=fluid velocity of the flow 110;
ρ=a density of a fluid present within the volume 260;
μ=a fluid velocity the fluid present in the volume 260; and
D=a diameter of the conduit 100.

By employing off-centre acoustic beams, for example ultrasonic beams, for interrogating the volume 260, namely region, information is obtained from the volume 260 which enables the aforesaid signal processing arrangement to perform uncertainty reduction computations, wherein:
(i) by employing interpolation of a detailed flow profile of the flow 110 for Reynolds number computation, an accurate flow profile calculation is possible, for example for determining whether the flow 110 is laminar or turbulent, also including a viscosity computation; and
(ii) computations can be performed for static and dynamic uneven flow velocities, for example for performing compensations for swirl and similar types of fluid motion within the volume 260. Such computations enable an onset of scale deposition within the conduit 100 to be identified.

In comparison, a known type of flow meter will generally propagate acoustic beams in a direction orthogonal to a wall of the conduit 100; the sensor apparatus 180 pursuant to the present disclosure employs non-orthogonal direction acoustic beams in addition of orthogonal acoustic beams, and thereby is able to extract more information from the volume 260 to determine its nature, for example whether it is laminar or turbulent due to scale build-up on the inside surface of the wall, as well as obtaining structural information which enables structural characteristics of the wall to be determined. Any gas introduced into a liquid phase present in the conduit 100 will result in an attenuation of the aforesaid acoustic beams; such measurement pertains:
(i) in situations of a liquid flow within the conduit 100;
(ii) in situations wherein multiphase flows occur within the conduit 100; and
(iii) in situations wherein gas flow with liquid fraction occurs in the conduit 100.

Thus, both off-centre and on-centre acoustic beam interrogation of the volume 260 is required for performing flow rate measurement involving a gas fraction in liquid, mutatis mutandis a liquid fraction present in a gas.

The sensor apparatus 180 pursuant to this disclosure is beneficially operable to employ at least three different strategies for non-invasive acoustic beam interrogation of the volume 260 by employing off-centre acoustic beams and/or interrogation of structural characteristics of the wall of the conduit 100, namely:
(a) an acoustic wide-beam interrogation of the volume 260, wherein "wide beam" corresponds for example to a beam 250 divergent angle of greater than 10°;
(b) a steered phase-array interrogation of the volume 260 and/or the wall of the conduit 100; and
(c) a measurement of transducer geometry and mounting orientation onto the conduit 100.

Optionally, shear-mode acoustic radiation generation is employed when implementing one or more of (a) to (c) within the sensor apparatus 180.

When wide-beam excitation is employed in the sensor apparatus 180, Lamb wave propagation is beneficially employed, wherein Lamb wave or wide beam sensors operate by emitting acoustic energy at various frequencies through the conduit 100 for locating a frequency which most closely matches a natural propagation frequency of acoustic radiation within a wall of the conduit 100. When the transducers 200, 300 are operated at such a matched frequency, acoustic radiation substantially at the matched frequency is transmitted into the flow 110 within the volume 260, with the wall of the conduit 100 functioning as a waveguide. As aforementioned, the wide beam of acoustic radiation travels outside the central axis of the conduit 100, and can be received at a convenient location using one or more of the transducers 300A, 300B, 300C. Optionally, as will be elucidated in greater detail later, the transducers 300A, 300B, 300C are beneficially implemented using Bragg-filter-grating transducers. Depending upon signals applied to the transducers 300A, 300B, 300C. acoustic modes can be selectively excited within the wall of the conduit 100 which are not coupled to the volume 260 and which are specifically useful for characterizing a structural integrity of the wall of conduit 100. Such selection is achieved by using an appropriate excitation frequency and steering beams of acoustic radiation so that they remain substantially within the wall of the conduit 100. The transducers 300A, 300B, 300C are capable of excite various acoustic modes more cleanly than has been hitherto possible, which are selectively steerable.

Figure 5:
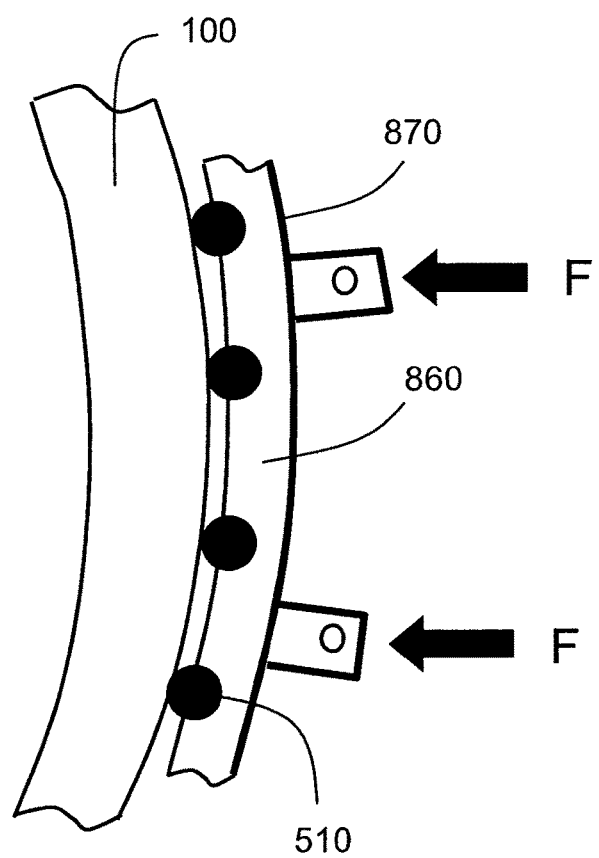
FIG. 5 is an illustration of a manner in which Bragg-filter-grating optical fibres are held in contact with a surface of a mechanical structure, for example onto an external surface of a conduit.

Acoustic radiation beam emissions from the transducers 200 are beneficially steered within the volume 260 and/or the wall of the conduit 100 by implementing the transducers 200 as phased arrays of acoustic emitting elements, for example driven by a plurality of signals S1 to S4 which are temporally shifted relative to one another to define a given angle of the beam 250 relative to the conduit 100 and its internal volume 260, or a direction of propagation within the wall of the conduit 100. Optionally, one or more elements of the phased arrays of elements forming the transducers 200 are assembled directly onto the external surface of the conduit 100, as illustrated in FIG. 4, or are assembled together into a transducer unit which is attached to the external surface of the conduit 100, for example as illustrated in FIG. 5.

Referring next to FIG. 3, an embodiment of the apparatus 180 is shown, wherein phased-arrays of elements are coupled to waveguides 200A, 200B, 200C to couple acoustic radiation into the volume 260 of the conduit 100 for steering acoustic radiation beams within the volume 260 and in the wall of the conduit 100 in operation, for example for providing one or more on-axis beams traversing the central axis of the conduit 100, as well as one or more off-axis beams, and as well as steering one or more beams within the wall of the conduit 100 for determining structural characteristics of the wall of the conduit 100, for example by way of selective mode attenuation and mode dispersion. Receiver transducers 300 are beneficially implemented in an array format, for example using a network of Bragg-grating-sensors based upon use of optical fibre components, as will be described in greater detail later. The waveguides 200A are optionally mounted in a spiral manner around the external surface of the conduit 100, as illustrated. Thus, the present disclosure includes adding guided-wave sensors in a grid configuration around the conduit 100 for picking up guided-wave signals from, for example, three sets of guided-wave transducers 200 in a 0°, 120° and 240° formation around the conduit 100, as illustrated.

Referring next to FIG. 4, there is shown an illustration of an alternative embodiment of the sensor apparatus 180, wherein three sets of guided wave transducers 200, are disposed at 120° angular positions around the conduit 100. Moreover surface mounted receiver transducers 300 are mounted at intervals around a circumference of the conduit 100 at a plurality of locations along a length of the conduit 100. The guide wave transducers 200 are intermingled with the receiver transducers 300, as illustrated. The receiver transducers 300 are beneficially implemented as a grid network of Bragg-grating filter transducers, for example mounted against the external surface of the conduit 100, or partially embedded into the external surface, for example in conformal reference indentations.

The receiver transducers 300, namely surface detectors, are located in three bands 400, 410, 420, substantially extending around a circumferential region of the conduit 100. First and third bands 400, 420 of the surface detectors are located areas from which guided acoustic waves from the transducers 200 of the transducers sets 200(1), 200(2), 200(3) hit the wall of the conduit 100 after reflection. A second band 410 of the surface detectors is located in an area in which the acoustic guided waves hit an opposite wall of the conduit 100.

Figure 8:
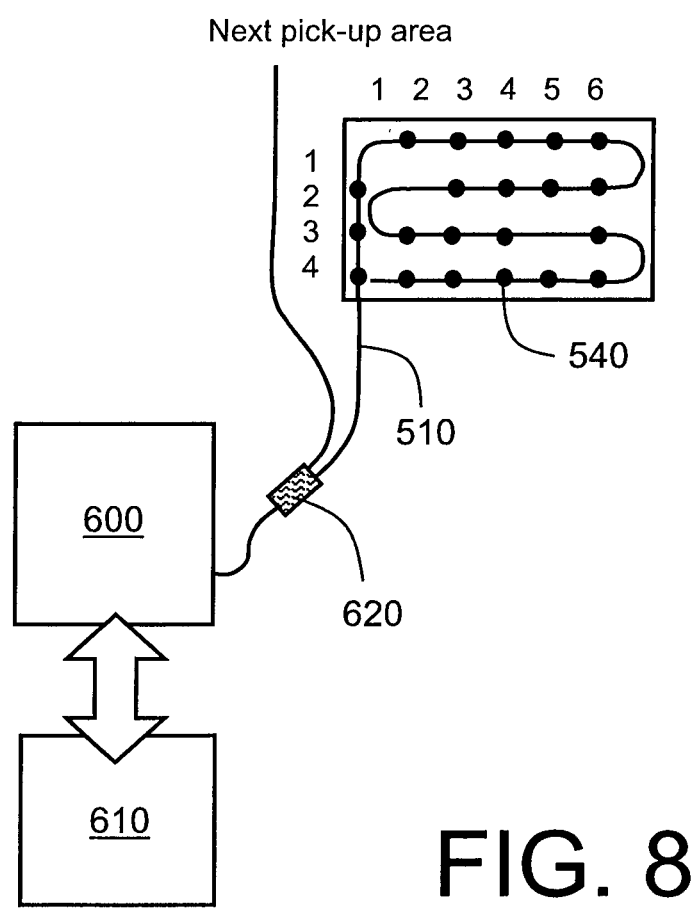
FIG. 8 is an illustration of an optical-fibre connection and data processing arrangement for use with the receiving transducers shown in FIG. 3 to FIG. 7.
Figure 9:
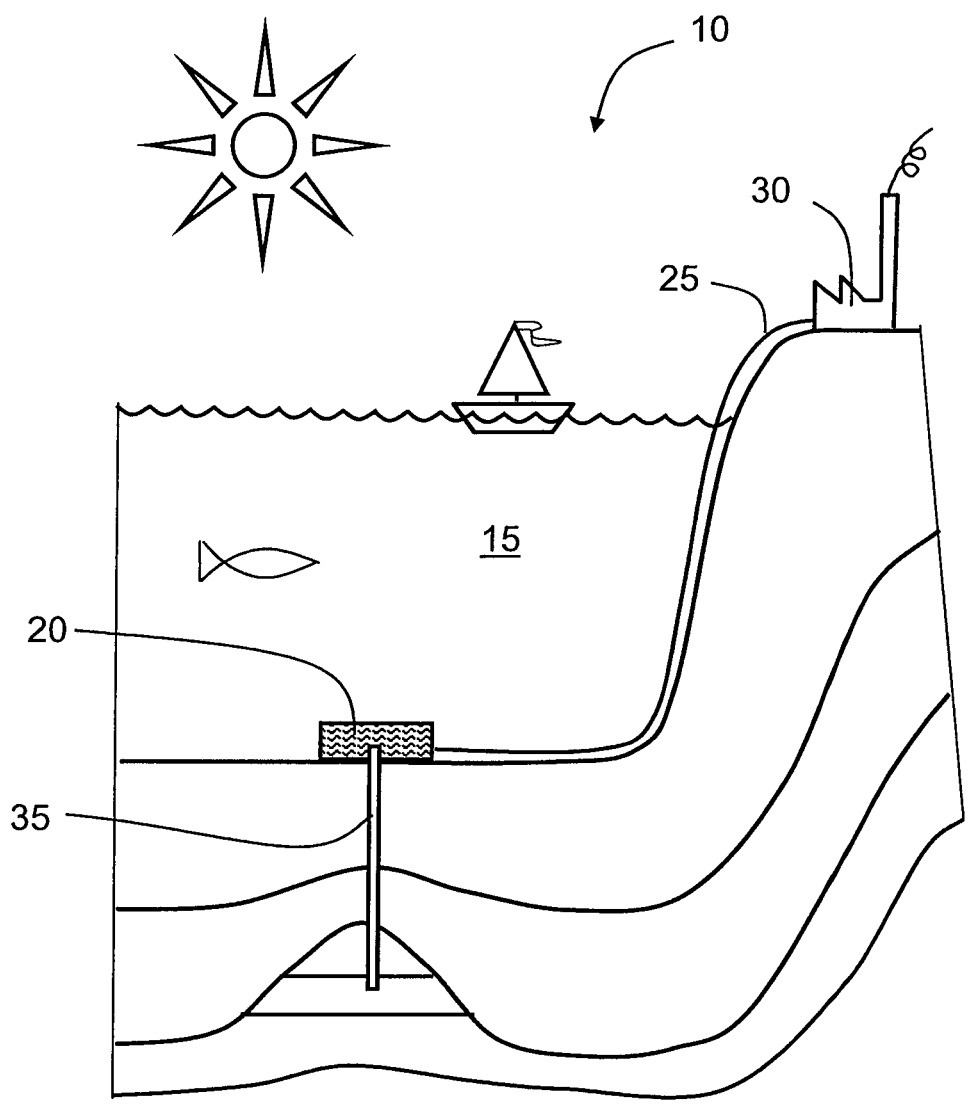
FIG. 9 is an illustration of an off-shore environment in which mechanical structural characteristics of a sea-bed arrangement and associated one or more pipelines are to be measured.

Referring next to FIG. 8, there is shown an illustration of the receiver transducers 300 for sensing an arrival of a wide acoustic beam emitted from the guided wave transducers 200; by "wide", is meant greater than 5° beam divergence angle, more optionally greater than 10° divergence angle. On account of the receiver transducers 300 being disposed in a circumferential manner around the external surface of the conduit 100 as shown, acoustic beams emitted from the three sets of transducers 200(1), 200(2), 200(3) are susceptible to being detected by the receiver transducers 300. Optionally, the receiver transducers 300 are implemented, as aforementioned, as a surface detector grid consisting of a plurality of acoustic detectors 540 having physical contact with the external surface of the wall of the conduit 100. Beneficially, the acoustic detectors 540 are connected to a signal processing arrangement, for example to a control unit wherein each detector 540 has an individual signal channel associated therewith. The acoustic detectors 450 are optionally implemented using aforesaid Bragg-grating filter sensors (Fibre Bragg Gratings, "FBG"), but are susceptible to being implemented in alternative manners, for example utilizing one or more of:
(i) piezo-electric transducers;
(ii) accelerometers;
(iii) microfabricated electronic mechanical devices (MEMs), for example micromachined microfabricated Silicon accelerometers and/or microphones;
(iv) any other type of substantially point sensor which is operable to detect acoustic radiation.

Bragg-grating filter sensors are especially beneficial in that multiple acoustic sensing points can be established along a length of a single optical fibre which is attached to the external surface of the conduit 100 to form a grid or band of sensors. Optical fibres are susceptible to high temporal rates of sensing, are insensitive to local electrical interference in operation, and are potentially very compact. Such compactness enables the acoustic detectors to be implemented using a plurality of optical fibres, thereby providing inbuilt redundancy in an event that one of the optical fibres were to fail when in service, for example in a sea-bed location, potentially several kilometers deep with ambient pressures in an order of 150 Bar or more.

Figure 2:
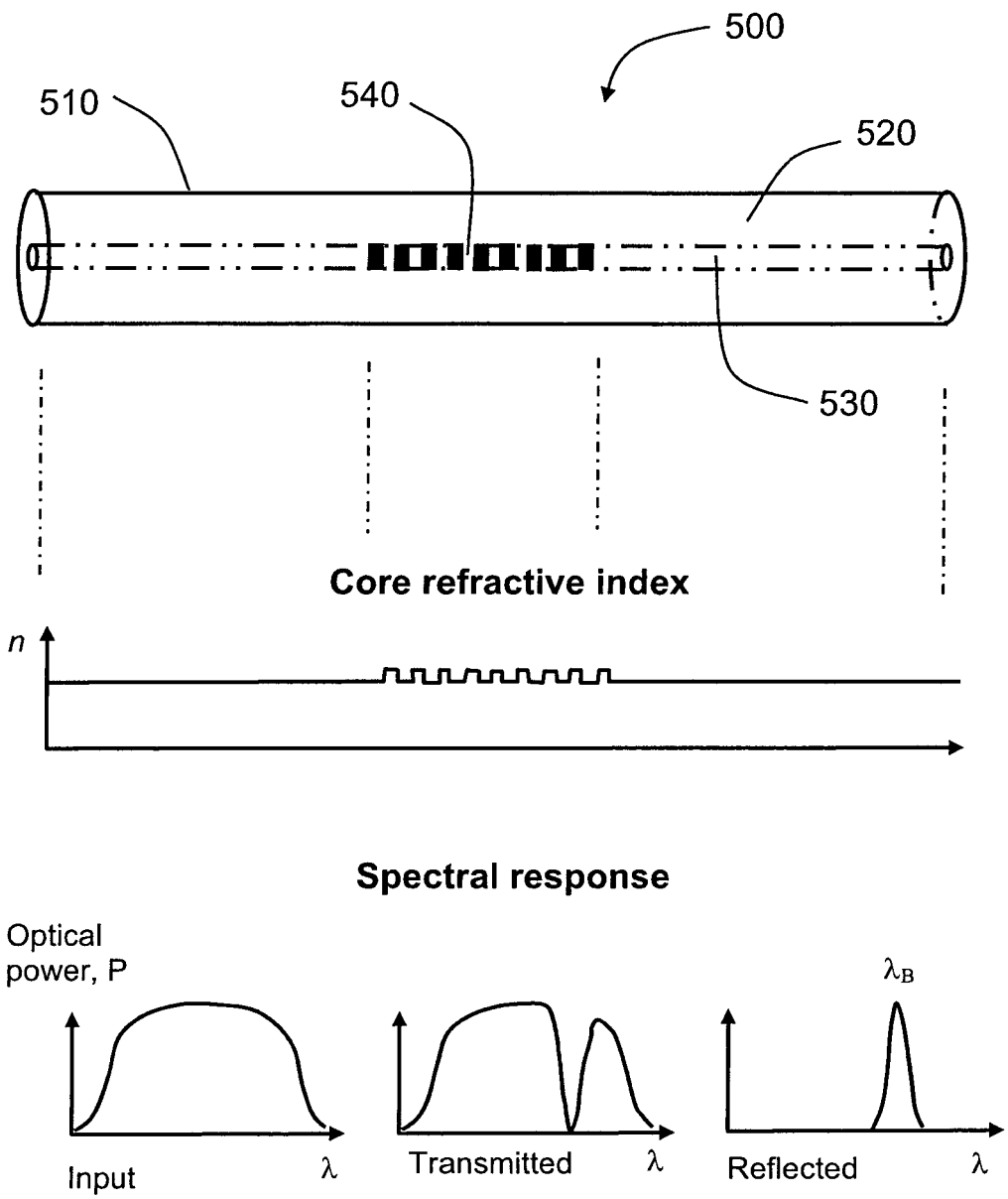
FIG. 2 is a schematic illustration of a sensor for use with the transducer arrangements of FIG. 1A, FIG. 2B, FIG. 1C, FIG. 1D and FIG. 1E.

Referring next to FIG. 2, there is shown a schematic illustration of a Bragg filter grating sensor indicated generally by 500; this sensor is also referred as being a "fibre Bragg grating sensor" (FBG). An optical fibre 510 includes an optical cladding 520 and an optical core 530. In operation, optical radiation propagates along the optical core 530 to which it is substantially confined by internal reflection occurring on account of the cladding 520 and the optical core 530 having refractive indexes $n_2$, $n_1$ respectively, wherein $n_2$ and $n_1$ are mutually different. The optical fibre 510 is optionally multi-mode optical fibre, alternatively mono-mode optical fibre. An optical grating 540 can be formed in the optical core by removing a portion of the cladding 520 in a region of the grating 540 to expose the optical core 530, by processing the optical core 530, for example by photolithographic steps followed by chemical or ion-beam milling, to modify its refractive index to form the grating 540, and then the removed cladding 520 restored by adding a polymer or glass material having a refractive index of substantially $n_2$. The grating 540 has a spatially varying refractive index having a period of $\lambda$, wherein optical radiation propagating in the optical core 530 have a wavelength therein similar to the period $\lambda$ experiences a point optical impedance mismatch, resulting in a portion of the optical radiation being reflected back along the optical fibre 510 as illustrated, and a correspondingly reduced amount of optical radiation being transmitted further along the optical fibre 510. As the grating 540 is stretched and compressed by acoustic radiation acting thereupon, the wavelength at which partial reflection of optical radiation occurs at the grating 540 is modified. Such a shift in wavelength, which is modulated by the received acoustic radiation at the grating 540, is detected in the aforesaid signal processing arrangement to generate a signal representative of the acoustic radiation received at the grating 540.

Referring next to FIG. 4, there is shown an illustration of the optical fibre 510 disposed upon the external surface of the conduit 100, disposed in a spatial region between the transducers 200A and 200B, wherein the transducers 200A, 200B corresponding to a set of transducers 200(1). The optical fibre 510 has a plurality of gratings 540 therealong. By meandering the optical fibre 510, a grid of detection points is established on the conduit 100 for detecting acoustic radiation thereat in operation. Beneficially, the optical fibre 510 is folded in a radius of curvature at ends of meanders which is greater than substantially fifteen times a diameter d of the optical fibre 510. Thus, one optical fibre is capable of addressing many individually-addressable acoustic radiation sensor points. Moreover, the optical fibre 510 can be coupled to the signal processing arrangement which is remote, for example a distance of 1 km or more remote from the gratings 540. A free-end of the optical fibre 510 which is remote from the signal processing arrangement is beneficially terminated in a substantially non-reflecting optical load, to prevent spurious reflections back-and-forth between ends of the optical fibre 510.

Referring next to FIG. 8, the signal processing arrangement if represented by a light source and a sensor 600, for example a solid-state laser, coupled to a photodiode detector, alternatively a Mach-Zehnder-based optical detector. Beneficially, the source and sensor 600 is coupled to a signal controller 610 for handling signals being input to and output from the source and sensor 600. As illustrated, the data processing arrangement, via an optical junction 620, is able to service several optical fibre 510 detector arrays attached to the external surface of the conduit 100. The optical fibre 510 is beneficially employed in petrochemical environments to reduce a risk of explosion hazard which may pertain to transducers which require directly-applied electrical signals for their operation. A 6×4 grid of gratings 540 is shown. The source and sensor 600, in combination with the signal controller 610 constitute a signal processing arrangement. The signal processing arrangement is beneficially, at least in part, implemented using computing hardware, for example one or more high-speed low-power-consumption RISC processors, for example manufactured by Arm (UK), which are able to process acoustic radiation signals in real-time, for example performing time-of-flight computations, correlations, convolutions and such like. The computing hardware is beneficially operable to execute one or more software products recorded on non-transient machine-readable data storage media, for example solid-state data memory, for implementing one or more algorithms for enabling the apparatus 180 to function as described.

Thus, a mounted sensor network as illustrated in FIG. 8 covers a significant number of positions around a cross-section of the conduit 100 in combination with three or more wide-team transducers 200, thereby sensing at many points within the region or volume 260. Information obtained from each wide-beam traverse enables the data processing arrangement to detect one or more of:

(i) characteristics of the flow 110, for example a fluid velocity of the flow 110;
(ii) a diameter of the conduit 100, for example for detecting corrosion, deposition, cracking, embrittlement on an inside surface of the conduit 100; and
(iii) a speed of acoustic radiation propagation within the region or volume 260.

As flow rate Q is defined by Equation 2 (Eq. 2):

$$Q = v*A \qquad \text{Eq. 2}$$

wherein
A=cross section area; and
v=flow velocity.

An error in computing A, namely internal area of the conduit 100, and the flow rate v as measured by the sensor apparatus 180, potentially results in an error when computing the flow rate Q. In order to account for tolerances of the conduit 100, for example in a retrofit situation, it is desirable to perform a calibration of the sensor apparatus 180. However, for new applications, it may be feasible to control dimensions of the conduit 100 more precisely, thereby potentially avoiding a need for such calibration of the sensor apparatus 180. However, it will be appreciated that the mounted sensor network provided by the optical fibre 510 in combination with three or more wide beams generated by the sets of transducers 200 enables such calibration to be implemented more precisely and reliably. Situation potentially arise for the sensor apparatus 180 that solid build-up in the conduit 100 occurs, resulting in a considerable change in effective pipe cross-section area, for example as illustrated in FIG. 11, situation C; for example, a 1 mm solid build up in a 2 inch (50 mm) diameter pipe represents a 4% reduction in the cross-sectional area of the conduit 100, and hence a corresponding 4% error in measurement of the flow rate Q. However, the sensor apparatus 180 is capable of correcting for such cross-sectional area by monitoring a dynamic effective cross-section of the conduit 100 by way of its multiple approaches to interrogating the region or volume 260.

Referring next to FIG. 12, there is shown an illustration of three pairs of Lamb-wave transducer configurations, for example using three sets of aforesaid transducers 200. Each pair of transducers 200 are operable to excite acoustic beams 250 in up-flow and down-flow directions, for example for making a differential measurement. When the flow 110 is homogeneous in which a gas bubble, for example the gas bubble 75 in FIG. 12, moves with a liquid flow, the sensor apparatus 180 is operable to perform following actions:

(i) to identify whether the fluid is predominantly water or oil, or a mixture of two liquid fractions;
(ii) to measure a flow velocity of the fluid flow 110;
(iii) to perform a liquid flow rate measurement through liquid velocity measurement, less gas bubble volume/velocity influences;
(iv) to identify an non-homogeneity as a gas bubble, for example the bubble 75; and
(v) to measure a velocity of the gas bubble, for example the gas bubble 700; and
(vi) to interrogate a wall the conduit 100 to determine its structural characteristics, wherein acoustic modes are selected for such characterization which are substantially limited to propagate within the wall. The structural characteristics include, for example wall thinning due to erosion and/or corrosion, build-up of scale or similar deposits, embrittlement and micro-cracking, for example resulting from the conduit 100 being subject to repetitive deformation due to excess pressure within the conduit 100.

The gas bubble, and any other similar gas bubbles present in the region or volume 260 of the conduit 100 will attenuate and/or scatter Lamb wave energy which is coupled from the transducer 200 through the wall of the conduit 100 into the region or volume 260. Beneficially, a pure liquid flow velocity is computed for a given situation by a computation of acoustic radiation transit time between transmitting and receiving transducers, namely between transducers 200A, 200B or 200, 300 as appropriate. A size of the bubble is determined by a size of acoustic "shadow" generated behind the bubble; such shadow is beneficially detected spatially using the transducer 300, namely grid array of gratings 540 disposed around the external surface of the conduit 100.

The transducer 300, for example implemented as the grid of grating sensors 540, enables spatial monitoring of the cross-section of the conduit 100 to be achieved, for example to detect regions of oil, water and gas, as well as structural characteristics of the wall of the conduit 100. Such cross-section monitoring, namely "tomographic monitoring", is achieved using multiple acoustic beams 250 from the three or more sets of transducers 200. Beneficially, following measurements are made using the apparatus 180 when in operation:

(i) a volume 810 between the transducer 200A and an area of reflection 820 at an opposite inside wall of the conduit 100; and
(ii) a volume 830 between the area of reflection 820 and an area whereat reflected acoustic radiation is received, for example at the transducer 200B.

Beneficially, such measurement is made for at least all three sets of transducers 200(1), 200(2), 200(3), thereby mapping six different regions of the region or volume 260, by way of the acoustic radiation being reflected at the inside wall of the conduit 100, as illustrated. Deposits of scale and/or occurrences of pitting due to erosion and/or corrosion to the wall of the conduit 100 are also susceptible to being detected by such tomography.

In the foregoing, various strategies for the sensor apparatus 180 to compute output indicate of flow rate and fractions present are described. In the following description, features of the sensor apparatus 180 will be described in greater detail. Referring to FIG. 3, the optical fibre 510 and its associated Bragg grating sensors 540 are employed to provide a surface-mounted sensor network which is capable of providing secondary outputs from the signal processing arrangement of the sensor apparatus 180, for example:

(a) a surface temperature profile of the conduit 100, for example for detecting a process malfunction or build-up of solid onto the inside surface of the conduit 100; and
(b) detecting changes in guided wave signal propagation directly though the wall of the conduit 100, as aforementioned, namely not via the region or volume 260, for detecting any changes in a structural integrity of the conduit 100, for example a material loss therefrom arising from erosion and/or corrosion, as well as fatigue damage, such as cracking of the wall of the conduit 100.

Referring next to FIG. 5, there is shown an illustration of a portion of the wall of the conduit 100 to which the optical fibre and its associated Bragg grating sensors 540 have been applied. Optionally, the optical fibre 510 is supported in a compliant backing material 860, for example fabricated from one or more polymeric materials, for example from a plastics material, which itself is supported onto a frame 870 to which a force F can be applied to ensure that the optical fibre 510 contacts onto the external surface of the conduit 100 in a stable and acoustically efficient manner. The backing material 860 is beneficially acoustically dissipative, likewise the frame 870, so that spurious acoustic radiation signals are not generated in the sensor apparatus 180 when in operation. In the apparatus 180, use of the transducers 200 potentially enhancing flow rate measuring accuracy for non-invasive acoustic radiation flow meters; such transducers 200 are beneficially also clamped or otherwise forced against the external surface of the conduit 100.

The aforesaid sensor apparatus 180 is capable of functioning as a pipe surface-mounted acoustic sensor grid for extending functionality of flow meters by measuring spatial flow information. As aforementioned, the apparatus 180 includes one or more, for example three, sets of transducers 200(1), 200(2), 200(3) mounted to the external surface of the conduit 100. The sets of transducers 200(1), 200(2), 200(3) are operable, when supplied with suitable drive signals, to generate Lamb waves within the wall of the conduit 100, wherein the Lamb waves are coupled into the region or volume 260 of the conduit 100 wherein fluid flows in operation, wherein the Lamb waves propagate as corresponding steered acoustic radiation in a form of one or more beams 250 which spread slightly as they propagate towards an opposite wall of the conduit 100. At an area of the opposite wall of the conduit 100 whereat the one or more beams 250 are received, there are included one or more receiver transducers 300, for example implemented as an acoustic sensor grid implemented using Bragg grating sensors 540 formed in an optical fibre 510 as aforementioned, which are operable of sensing an arrival of a representative number of beams 250 of acoustic radiation propagating though the volume 260. The one or more receiving sensors 300 detect differences in properties of the one or more beams 250 of the acoustic radiation which arrive, for example in respect of their received amplitude and their time-of-flight, for an entire area in which the acoustic radiation propagates.

The acoustic radiation is reflected from the opposite wall and propagates through a further spatial volume within the volume or region 260, eventually arriving at a same side of the pipe from which the one or more beams 250 were originally emitted. On the same side, the one or more beams of acoustic radiation are received by one or more receiver transducers 300 and/or one of the transducers 200 of the sets 200(1), 200(2), 200(3) being employed. Optionally, by measuring the amplitude of a portion of the acoustic radiation emitted out to the opposite wall of the conduit 100 that is received back on the same side of the wall of the conduit 100, a fluid phase at a position of the transducers 200, 300 can be determined, as more energy is reflected in a presence of gas at the inner surface of the wall of the conduit 100.

Optionally, the distributed receiver transducers 300, for example implemented as Bragg grating filter sensors 540, detect changes in properties relating fluids flowing through the conduit 100, for example solid transport in aforesaid fluids, wherein the solid is a wax, a hydrate, scale, in addition to a surface temperature of the conduit 100. Such information to be derived from primary steered acoustic radiation beams, and/or from secondary acoustic radiation, for example shear mode excitation and acoustic radiation by additional transducers added to the sensor apparatus 180.

Optionally, the receiver transducers 300, for example Bragg grating filter sensors 540, are employed to detect dimension of the conduit 100, for determining pipe degradation such as wall thinning, corrosion, erosion, cracking, pitting pipe coating thickness and other pipe integrity issues. Such information is beneficially derived primary steered acoustic radiation beams which are excited in the sensor apparatus 180, in addition to secondary acoustic radiation, for example shear mode excitation and acoustic radiation by additional transducers added to the sensor apparatus 180.

Optionally, the sensor apparatus 180 is implemented by using one central controller for synchronizing all three or more transducers 200 and their associated surround receiver sensors 300. Spatial information, obtained via use of these transducers 200, 300 for interrogating the region or volume 260 of the conduit 100 through use of synchronous and repetitive excitation, enables laminar, transitional and turbulent multiphase flows within the conduit 100 to be analyzed. As described in the foregoing, at least six regions of the volume or region 260 are interrogated by the steered beams 250, when three transducers 200 are employed; optionally, these six regions are at least partially spatially overlapping. Fluid phase fraction % and a flow rate across a full cross-section of the volume or region 260 can be determined using the sensor apparatus 180. When gas bubbles present within the conduit 100 causes attenuation of acoustic radiation propagating therein, the receiver transducers 300, for example implemented as a spatially-distributed grid of sensors 540, off-centre propagation of acoustic radiation is measured and shadowing caused by the gas bubbles is detected. Optionally, the transducers 200 are beneficially excited at two or more frequencies in a sequential manner, for reducing uncertainty in measured signals, and thereby increasing measurement accuracy of the sensor apparatus 180.

Next, the sets of transducers 200 implemented will now be elucidated in greater detail. Referring to FIG. 3, the sets of transducers 200 are operable to direct and shape selected acoustic propagation modes for the aforesaid acoustic radiation, thereby ensuring improved utilization of emitted acoustic radiation within the conduit 100. The acoustic radiation 240, propagating for example as beams 250, is directed towards a similarly shaped receiving transducer 200; for example, the transducer 200A emits the acoustic radiation, and the transducer 200B receives the acoustic radiation after it has been reflected from an opposite wall of the conduit 100 relative to that on which the transducers 200A, 200B are mounted, as illustrated. Such a structure for the transducers 200A, 200B enables radiation corresponding to spurious unwanted acoustic radiation propagation modes to be rejected and thus not contribute to received acoustic radiation signals, as represented by output signals from the transducer 200B, in this example, thus increasing measurement signal-to-noise ratio and hence enhancing measurement accuracy.

In the transducers 200A, 200B, the waveguide therein is substantially untapered, namely is different to a conventional wedge-shape coupling element used to couple ultrasonic transducers to an external surface of a conduit, a plate, a tank or similar or pipe, for example in a manner of shear wave propagation; in contradistinction to such conventional wedge-shape coupling element, the transducers 200A, 200B are operable to excite selectively many mutually different types of modes, and also are operable to receive selectively many mutually different types of modes. Such mode selection enables a comprehensive structural characterization of the wall of the conduit 100, of a planar structure, and other flat or curved structures feasible. Temporal changes in such mutually different mode propagation, and associated mode dispersion, provides valuable information which is indicative, for example, of structural integrity. The waveguide of the transducers 200A, 200B is capable of reducing signal drifts in signals obtained in the sensor apparatus 180 that would otherwise arise if wedge-shaped coupling elements were employed. Moreover, the waveguide of the transducers 200A, 200B is capable of coupling acoustic radiation more efficient to and from the wall of the conduit 100, on account of coupling radiation to and from the wall of the conduit 100 over an extensive area of the conduit 100, in contradistinction to conventional wedge-type transducers which provide substantially a point coupling of shear wave acoustic radiation. Furthermore, the elongate length of the waveguide of the transducers 200A, 200B, in conjunction with associated monitoring sensors 230 enables an acoustic velocity within the transducers 200A, 200B to be determined, thereby enabling a temperature compensation of transducer 200 characteristics to be performed by the data processing arrangement of the sensor apparatus 180. Additionally, the monitoring sensors 230 enable operating integrity of the transducers 200A, 200B to be verified, for example equipment failure detection, which may be potentially relevant when the sensor apparatus 180 is a critical part of a petrochemicals facility, materials processing facility, power station, nuclear facility and similar.

Referring next to FIG. 1A, there is shown a detailed diagram of an example of the transducers 200, wherein the transducer 200 is shown mounted to an external surface of the wall of the conduit 100. The transducer includes an elongate waveguide 200A which is susceptible to being implemented in several ways, for example:

(a) as an elongate helix for exciting one or more helical modes of acoustic wave propagation within the wall of the conduit 100;

(b) as a substantially straight bar, a strip, an elongate plate, a flared plate;

(c) as a curved straight bar, a strip, an elongate plate;

(d) as a collar, as a flared collar; and (e) as an annulus.

The waveguide 200A includes a neck region 228 which is beneficially curved so as to provide improved matching and less mode dispersion within the waveguide 200A.

The waveguide 200A has a thickness $h_{w1}$ which is substantially similar to a thickness $h_{w2}$ of a wall of the conduit, a plate or similar to which the waveguide 200A is mounted. Beneficially, the waveguide 200A is fabricated from a substantially similar material to that of the wall of the conduit 100, or from a material which has substantially similar material mechanical characteristics to that of the wall of the conduit 100. The waveguide 200A is beneficially manufactured from a metal, an alloy, a sintered material, a ceramic material, a composite material, a piezoelectric ceramic material, but not limited thereto. Moreover, the waveguide 200A is optionally integral with the wall of the conduit 100, for example machined from a mutually common component. Furthermore, the waveguide 200A is optionally a clamp-on device wherein a coupling cement, adhesive or gel is optionally used to provide an acoustic interface from the waveguide 200A to the wall of the conduit 100.

The waveguide 200A beneficially has a height:length aspect ratio, namely $L_{w1}$:$h_{w1}$ ratio, in a range of 1.5:1 to 20:1, more optionally in a range of 2:1 to 10:1. Moreover, the waveguide 200A beneficially has a width:height ratio, namely $b_{w1}$:$h_{w1}$ in a range of 2:1 to 1:100, and more optionally in a range of 1:1 to 1:20.

The waveguide 200A is coupled via a neck region 228 to a distal end indicated generally by 220. At the distal end 220, there is mounted, or otherwise provided, a cluster of elements 225, wherein at least one element is included on an end face of the distal end, as shown, and one or more elements are included on one or more side faces of the distal end as illustrated. Optionally, elements are mounted on a plurality of side faces of the distal end, as illustrated. The elements are beneficially implemented as piezoelectric elements when the transducer is required to excite acoustic radiation. When the transducer is to receive acoustic radiation, the elements 225 are optionally implemented as piezoelectric receiver elements and/or optical fibre Bragg-grating sensors.

The element at the end face of distal end is selective excited in operation to excite shear waves within the waveguide 200A. When the element on an upper or lower side face of the distal end is excited at relatively high frequencies, for example in an order of 1 MHz, Rayleigh are excited in operation within the waveguide 200A. Moreover, when a combination of drive signals is applied to the element at the end face of the distal end and to one or more of the elements at side faces of the distal end, a steerable mode is generated within the waveguide 200A, which can be used to generate a steerable beam of radiation within the volume 260 of the conduit 100, or confined to the wall of the conduit 100 in a steerable manner. Such multimode operation of the waveguide 200A is not feasible with known types of ultrasonic transducers which are predominantly shear mode type transducers.

The neck region 228 is beneficially considerable shorter than the waveguide 200A itself, for example at least five times shorter. Optionally, the distal end is raised, as illustrated, to enable a shield 235 to be inserted between the distal end and the outer surface of the wall of the conduit 100. The shield 235 is beneficially a thermal shield and/or ionizing radiation shield. When a thermal shield is required, the shield 235 is beneficially implemented as a multilayer structure including reflective electrical conductive layers, for example fabricated from metal film, grapheme film or similar, sandwiched between dielectric layers. Alternatively, when ionizing radiation shielding is required, the shield 235 is fabricated from a material including radiation absorbers such as lead, bismuth, boron, xenon, or similar; xenon is absorbed into interstitial spaces in certain materials and becomes physically trapped in interstitial spaces; for ionizing radiation shielding, silicon carbide is beneficially employed as a structural component of the shield 235, on account of its ability mechanically to resist neutron embrittlement.

The waveguide 200A is also provided with a sensor arrangement 230 for monitoring acoustic modes that are excited within the waveguide 200A, when in operation. The sensor arrangement 230 is optionally implemented using one or more piezoelectric elements or Bragg-grating sensors, as described in the foregoing. The Bragg-grating sensors are beneficially included a mutually common optical fibre which is formed in multiple pigtail loops for provided a linear array of sensor elements for the sensor arrangement; this represents a particularly compact and effect manner of implementing the sensor arrangement 230. The sensor arrangement 230 enables corrections to be made to mode steering direction and/or mode amplitude, for example for errors arising from gradual depolarization of the piezoelectric elements disposed at the distal end of the waveguide 200A.

Referring next to FIG. 1B, the waveguide 200A is beneficially implemented in a symmetrical manner, wherein a first distal end includes the elements 225 for exciting acoustic radiation, for example an element 225B at an end face of the first distal end and an element 225A on a side upper face of the first distal end, and a second distal end includes a similar arrangement of elements 240, for example an element 240B at an end face of the second distal end and an element 240A on a side upper face of the first distal end. As aforementioned, these elements are beneficially driven selectively at the first distal end to excite selected acoustic modes, and monitored at the second distal end to verify an amplitude and steering direction of the excited acoustic radiation in the waveguide 200A. Optionally, the first and second distal ends are raised away from the external surface of the conduit 100 to enable the shield 235 to be interposed for providing shielding for the elements. The shield 235 is optionally extended to provide protection from an ambient environment surrounding the waveguide 200A.

Referring next to FIG. 1C, the waveguide 200A is further provided with an active acoustic damping arrangement at the second distal end, wherein the elements 240A and 240B are employed to sense acoustic modes generated by the elements 225 within the waveguide 220A, and the elements 240C, for example implemented as piezoelectric elements, are driven with selected anti-phase drive signals for dampening reflection of acoustic radiation being reflected at the end face of the second distal end which could otherwise cause formation of a standing wave mode within the waveguide 200A between the end faces of the first and second distal ends. Optionally, passive damping materials are added at the second distal end to dampen reflection of radiation from end faces of the first and second distal ends; such damping materials include, for example elastic polymeric material, resins, waxes, gels and similar.

As aforementioned, the waveguide 200A can be shaped as an elongate strip, a helical strip, a flat plate, a flared plate, a curved plate, a collar, a flared collar, an annulus, or similar. Moreover, the waveguide 200A is optionally shaped so as to be capable of supporting only a limited number of different acoustic modes, for example by making it long relative to its width, and having a low aspect ratio for its height relative to its breadth. Alternatively, the waveguide 200A can be implemented as a broad strip which is capable of supporting a large number of acoustic modes, when a higher degree of acoustic mode steerability is required. Optionally, the waveguide 200A is tapered along its length, between its one or more necks 228, namely a principal length $L_{w1}$ of the waveguide 200A. Alternatively, the waveguide 200A can have a substantially constant cross-section along its length, between its one of more necks 228.

Referring to FIG. 1D, there is provided an illustration of the waveguide 200A as a broad strip, wherein the elements 225 are implemented as a phased array for enabling an excited mode of acoustic radiation 238 to be steered in a range of angles θ, by varying at least one of:
(a) a frequency of drive signals applied in operation to the elements 225;
(b) a relative phase of drive signals applied in operation to the elements 225; and
(c) a relative amplitude of drive signals applied in operation to the elements 225

Figure 1E:
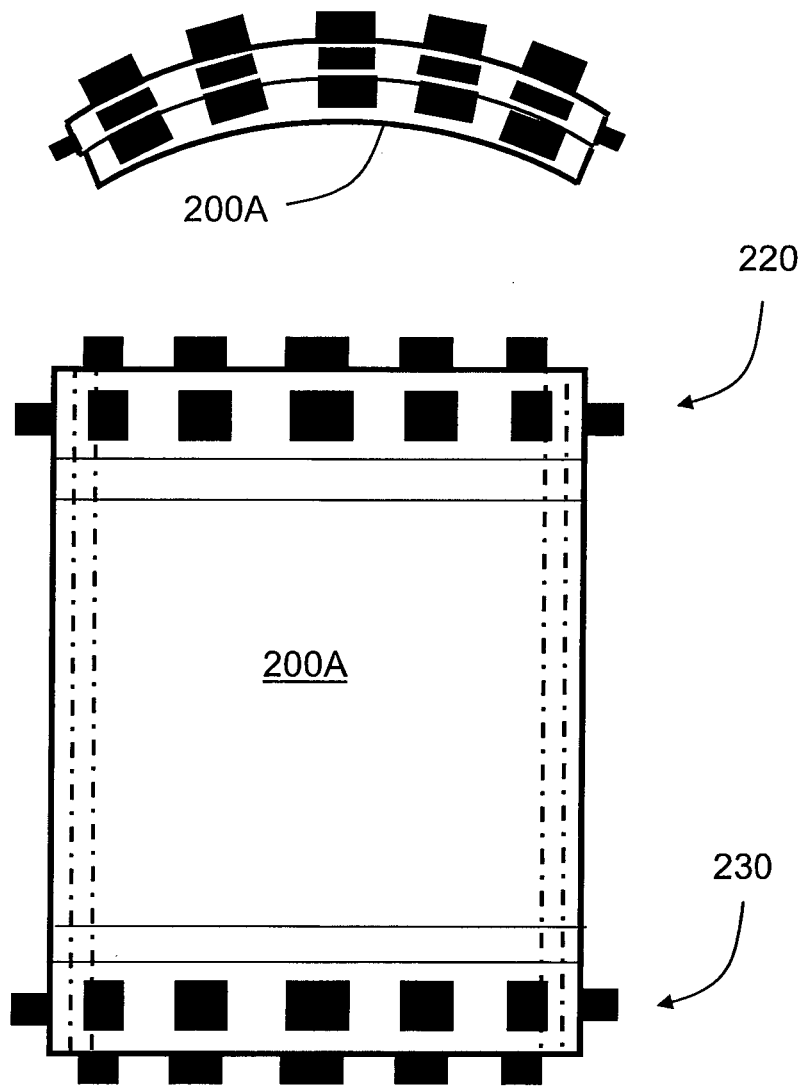

Referring to FIG. 1E, the waveguide 200A, is optionally broad and curved in form, for example for being detachable mountable to the conduit 100, and being operable to excite a beam of a mode of highly pure acoustic radiation for interrogating, for example the wall of the conduit 100, and optionally a region adjacent thereto.

Referring next to FIG. 13, there is shown a pipeline as described in the aforementioned published patent document WO2014/098613A1 ("Sensor System for Corrosion Monitoring", applicant—TeCom AS), which is hereby incorporated by reference. In this published document, there is described a sensor system for monitoring corrosion in a wall of a pipeline or vessel, indicated generally by 1000 in FIG. 13. The pipeline or vessel 1000 includes the conduit 100 which is surrounded by cladding 1010; the cladding 1010 is, in turn, surround by an outer protection layer 1020. The sensor system includes at least one acoustic emitter. Moreover, the sensor system includes an optical fibre provided with an arrangement for converting an acoustic signal to a corresponding optical signal. During operation, the at least one acoustic emitter emits a beam of acoustic radiation which is then reflected as a corresponding reflected beam which is received by the optical fibre to provide information for the optical signal. A sensitive material of the optical fibre allows for corrosion-related chemical parameters to be measured in a continuous fashion over a length of the optical fibre. The chemical parameters relate to at least one of: liquid water, humidity, salinity, pH and electrical conductivity. The arrangement for converting the acoustic signal to the corresponding optical signal is based upon the use of Bragg filter gratings.

The waveguide 200A, for example as illustrated in FIG. 1A, FIG. 1B, FIG. 1C, FIG. 1D or FIG. 1E is beneficially employed for the aforesaid acoustic emitter in the pipeline or vessel 1000. Moreover, sensors of the waveguide 200A implemented for sensing acoustic modes generated therein are beneficially includes in a common optical fibre which also provides for optical Bragg-filter sensors included in the cladding 1010, and/or included in a region between an inner surface of the cladding 1010 and an external surface of the wall of the conduit 100. Use of the waveguide 200A enables improved steering of acoustic modes for PIMSCUI purposes, namely corrosion under insulation monitoring, to be achieved. An appropriate signal processing arrangement, denoted by 600, 610, is beneficially provided to excite elements 225 of the waveguide 200A, and to process received signals from the Bragg-filter sensors, denoted by 540, to provide an output signal indicative of mechanical structural characteristics of the conduit 100, for example a risk or onset of corrosion and/or leakage occurring. Optionally, the signal processing arrangement employs a look-up table, a numerical physical model and/or neural network analysis of signals received from the Bragg-filter sensors for provided an analysis or diagnosis of the mechanical structural characteristics of the conduit 100, for example temporal changes in characteristics of the conduit 100 and an associated physical significance thereof, for example thinning, corrosion, embrittlement, leakage, scale deposition within the conduit 100, and so forth.

Modifications to embodiments of the invention described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The invention claimed is:

1. A sensor apparatus for measuring characteristics of a wall of a structure and/or a medium in contact with the structure, wherein the sensor apparatus includes a transducer arrangement disposed in operation at least partially around a planar or curved surface of the wall of the structure, or disposed over a region of a planar or curved surface of the wall of the structure, wherein:
the sensor apparatus includes a transducer waveguide including at least one free distal end whereat one or more driver elements are mounted on the at least one free distal end, wherein the at least one free distal end includes a neck region which is operable to couple one or more Lamb modes of propagation between the one or more driver elements and a remainder of the transducer waveguide in contact with the wall of the structure;
wherein the neck region and the remainder of the transducer waveguide have a substantially similar thickness to the wall of the structure, and is fabricated from a material which is substantially similar to that of the wall of the structure, wherein the neck region and the remainder of the transducer waveguide have substantially similar acoustic dispersion characteristics as the wall of the structure; and
wherein the one or more driver elements are operable to excite an acoustic Lamb mode propagation within the wall of the structure, via the Lamb wave propagation in the transducer waveguide, for providing information indicative of properties of the wall and/or material present in the vicinity of the wall which interacts with the acoustic Lamb wave propagation in the wall of the structure.

2. The sensor apparatus as claimed in claim 1, wherein the transducer waveguide is operable to excite a helical acoustic Lamb wave propagation in the wall of the structure, wherein the structure is a pipe, and the transducer waveguide is curved about the pipe.

3. The sensor apparatus as claimed in claim 1, wherein the one or more driver elements of the transducer waveguide are operable to select one or more specific Lamb modes of the acoustic Lamb wave propagation by exciting a predominantly through-thickness stress/displacement signature for the one or more specific Lamb modes.

4. The sensor apparatus as claimed in claim 3, wherein the one or more driver elements are configurable by selectively exciting them to switch between the one or more specific Lamb modes.

5. The sensor apparatus as claimed in claim 1, wherein the or more driver elements are disposed in a phase array configuration.

6. The sensor apparatus as claimed in claim 1, wherein an amplitude of one or more of the Lamb modes excited in the transducer waveguide are monitored by an additional one or more sensors attached to the transducer waveguide.

7. The sensor apparatus as claimed in claim 1, wherein the one or more driver elements are provided with a shielding arrangement for shielding them from thermal and/or ionizing radiation emitted from the structure.

8. The sensor apparatus as claimed in claim 1, wherein the transducer waveguide is detachably mountable to the structure.

9. The sensor apparatus as claimed in claim 1, wherein the sensor apparatus includes a data processing arrangement for generating drive signals to drive the one or more driver elements for selectively interrogating one or more regions adjacent to the wall of the structure, and the data processing arrangement is operable to receive signals from the one or more regions, and to perform tomographic computation upon the data to identify, in respect of the wall, at least one of: a scale hydrate deposit on the wall, erosion and/or corrosion of the wall, cracking of the wall.

10. The sensor apparatus as claimed in claim 1, wherein the sensor apparatus further includes one or more environmental sensors disposed in a region between an outer surface of the wall of the structure and a cladding of the structure, wherein the one or more environmental sensors are disposed remotely in respect of the transducer waveguide and are operable to receive acoustic radiation coupled along the wall of the structure to the one or more environmental sensors.

11. The sensor apparatus as claimed in claim 10, wherein the environmental sensors are operable to measure chemical parameters relating to at least one, of: liquid water, humidity, salinity, pH and electrical conductivity.

12. The sensor apparatus as claimed in claim 10, wherein the transducer waveguide and the one or more environmental sensors employ a common optical fibre with the one or more environmental sensors formed therealong for sensing purposes.

13. The sensor apparatus as claimed in claim 1, wherein the transducer arrangement includes a spatially distributed array of sensors disposed on an external surface of the wall for receiving acoustic radiation coupled through the wall thereto and wherein the spatially distributed array of sensors is implemented using a plurality of Bragg grating filter sensors distributed along one or more optical fibres, wherein the Bragg grating filter sensors are optically interrogated in operation via optical radiation guided through the one or more optical fibres and selectively reflected and/or transmitted at the Bragg grating filter sensors.

14. The sensor apparatus as claimed in claim 13, wherein the spatially distributed array of sensors is interspersed between the transducer waveguide of the transducer arrangement for generating one or more beams.

15. The sensor apparatus as claimed in claim 1, wherein the transducer arrangement includes one or more interfacing components which enabled the transducer arrangement to be excited from one or more optical signals conveyed via one or more optical fibres coupled to the sensor apparatus and/or to output its received acoustic radiation signals via the wall in an optical form via one or more optical fibres.

16. The sensor apparatus as claimed in claim 15, wherein the one or more interfacing components are based on a use of Silicon Carbide semiconductor devices.

17. The sensor apparatus as claimed in claim 1, wherein the sensor apparatus is adapted to operate in one or more of: petrochemical facilities, chemical processing facilities, nuclear energy facilities, fermentation tank facilities, food processing facilities, water treatment facilities, and waste treatment facilities.

18. The sensor apparatus as claimed in claim 1, wherein the sensor apparatus is arranged to operate such that:
   (a) a plurality of beams are arranged to interrogate sampling points off-axis and on-axis in a cross-section of a region for determining whether a flow therein is laminar, transitional or turbulent;
   (b) the plurality of beams are employed in a repetitive manner to monitor temporal fluctuations in the flow;
   (c) the transducer arrangement is operable to sense spatially varying attenuation of a received acoustic radiation thereat for determining an occurrence of one or more gas volumes present within the region;
   (d) the transducer arrangement is employed for performing time-of-flight measurements for propagation of the received acoustic radiation within the region in upstream and downstream flow directions; and
   (e) the transducer arrangement is coupled to a corresponding signal processing arrangement for exciting the transducer arrangement and for processing received signals generated by the transducer arrangement to provide measurement output data representative of at least one of: flow velocity within the region, an indication of phases present in the region, a flow rate through the region.

19. A method of using a sensor apparatus for measuring characteristics of a wall of a structure and/or a medium in contact with the structure, wherein the sensor apparatus includes a transducer arrangement disposed in operation at least partially around a planar or curved surface of the wall of the structure, or disposed over a region of a planar or curved surface of the wall of the structure, wherein the method includes:
   (i) arranging for the sensor apparatus to include a transducer waveguide including at least one free distal end whereat one or more driver elements are mounted on the at least one free distal end, wherein the at least one free distal end includes a neck region which is operable to couple one or more Lamb modes of propagation between the one or more driver elements and a remainder of the transducer waveguide in contact with the wall of the structure;
   (ii) arranging for the neck region and the remainder of the transducer waveguide to have a substantially similar thickness to the wall of the structure, wherein the neck region and the remainder of the transducer waveguide is fabricated from a material which is substantially similar to that of the wall of the structure;
   (iii) arranging for the neck region and the remainder of the transducer waveguide to have substantially similar acoustic dispersion characteristics as the wall of the structure; and
   (iv) operating the one or more driver elements to excite an acoustic Lamb wave propagation within the wall of the structure, via the Lamb mode propagation in the transducer waveguide, for providing information indicative of properties of the wall and/or material present in the vicinity of the wall which interacts with the acoustic Lamb wave propagation, in the wall of the structure.

20. A computer program product comprising a non-transitory computer-readable data storage medium having computer-readable instructions stored thereon, the computer-readable instructions being executable by a computerized device comprising processing hardware to perform the actions of:

arranging for the sensor apparatus to include a transducer waveguide including at least one free distal end whereat one or more driver elements are mounted on the at least one free distal end, wherein the at least one free distal end includes a neck region which is operable to couple one or more Lamb modes of propagation between the one or more driver elements and a remainder of the transducer waveguide in contact with a wall of the structure;

arranging for the neck region and the remainder of the transducer waveguide to have a substantially similar thickness to the wall of the structure, wherein the neck region and the remainder of the transducer waveguide is fabricated from a material which is substantially similar to that of the wall of the structure;

arranging for the neck region and the remainder of the transducer waveguide to have a substantially similar acoustic dispersion characteristic as the wall of the structure; and operating the one or more driver elements to excite an acoustic Lamb wave propagation within the wall of the structure, via the Lamb mode propagation in the transducer waveguide, for providing information indicative of properties of the wall and/or material present in the vicinity of the wall which interacts with the acoustic Lamb wave propagation, in the wall of the structure.

21. The sensor apparatus as claimed in claim 1, wherein the neck region is operable to couple $A_0$ Lamb modes between the one or more driver elements and a remainder of the transducer waveguide in contact with the wall structure, wherein the at least one or more driver element is operable to excite an acoustic $A_0$ Lamb wave propagation for providing the information indicative of the properties of the wall and/or material present in the vicinity of the wall which interacts with the acoustic $A_0$ lamb wave propagation.

* * * * *